United States Patent
Siff

(10) Patent No.: US 11,813,450 B2
(45) Date of Patent: Nov. 14, 2023

(54) WEARABLE SYSTEM FOR AN ELECTROTHERAPY DEVICE

(71) Applicant: BioWave Corporation, Norwalk, CT (US)

(72) Inventor: Bradford Siff, Norwalk, CT (US)

(73) Assignee: BioWave Corporation, Norwalk, CT (US)

( * ) Notice: Subject to any disclaimer, the term of this patent is extended or adjusted under 35 U.S.C. 154(b) by 126 days.

(21) Appl. No.: 17/186,807

(22) Filed: Feb. 26, 2021

(65) Prior Publication Data

US 2021/0178158 A1 Jun. 17, 2021

Related U.S. Application Data

(63) Continuation-in-part of application No. 16/661,728, filed on Oct. 23, 2019, now Pat. No. 11,633,594.

(60) Provisional application No. 62/749,233, filed on Oct. 23, 2018.

(51) Int. Cl.
*A61N 1/36* (2006.01)

(52) U.S. Cl.
CPC ..... *A61N 1/36021* (2013.01); *A61N 1/36031* (2017.08); *A61N 1/36034* (2017.08)

(58) Field of Classification Search
CPC ............ A61N 1/36021; A61N 1/36031; A61N 1/36034
USPC .......................................................... 607/46
See application file for complete search history.

(56) References Cited

U.S. PATENT DOCUMENTS

| | | | |
|---|---|---|---|
| 5,397,338 | A | 3/1995 | Grey et al. |
| 6,584,358 | B2 | 6/2003 | Carter et al. |
| 6,760,627 | B2 | 7/2004 | Carter et al. |
| 6,792,315 | B2 | 9/2004 | Carter et al. |
| 6,853,863 | B2 | 2/2005 | Carter et al. |
| 7,013,179 | B2 | 3/2006 | Carter et al. |
| 7,130,696 | B2 | 10/2006 | Carter et al. |
| 2005/0033381 | A1 | 2/2005 | Carter et al. |

(Continued)

FOREIGN PATENT DOCUMENTS

| WO | 2020072128 A1 | 4/2020 | |
|---|---|---|---|
| WO | WO-2020072128 A1 * | 4/2020 | ............. A61B 5/389 |

OTHER PUBLICATIONS

International Search Report and Written Opinion of PCT/US2022/016413 Issued by the International Searching Authority; dated May 12, 2022, Entire Document.

*Primary Examiner* — Aaron F Roane
(74) *Attorney, Agent, or Firm* — Duane Morris LLP

(57) ABSTRACT

A wearable garment may have a flexible material configured to wrap around a portion of a user's body. The flexible material may have an interior surface configured to contact the user's body and an opposite exterior surface. The garment may further have a first electrode positioned at the interior surface and configured to contact a targeted part of the user's body and a second electrode positioned at the interior surface and configured to contact a targeted part of the user's body. The garment may also have a first electrode connector positioned at the exterior surface and operably connected to the first electrode and a second electrode connector positioned at the exterior surface and operably connected to the second electrode. The first and second electrodes are configured to deliver a therapeutic signal from an electrotherapeutic device via the first and second electrode connectors.

22 Claims, 34 Drawing Sheets

(56) References Cited

U.S. PATENT DOCUMENTS

| | | |
|---|---|---|
| 2005/0187591 A1 | 8/2005 | Carter et al. |
| 2007/0016268 A1 | 1/2007 | Carter et al. |
| 2008/0033492 A1 | 2/2008 | Siff et al. |
| 2008/0097530 A1* | 4/2008 | Muccio ............... A61N 1/36021 607/46 |
| 2010/0234919 A1 | 9/2010 | Minogue et al. |
| 2016/0121099 A1* | 5/2016 | Kiani ................... A61N 1/3603 607/48 |
| 2020/0121925 A1 | 4/2020 | Siff et al. |
| 2021/0178158 A1 | 6/2021 | Siff |

* cited by examiner

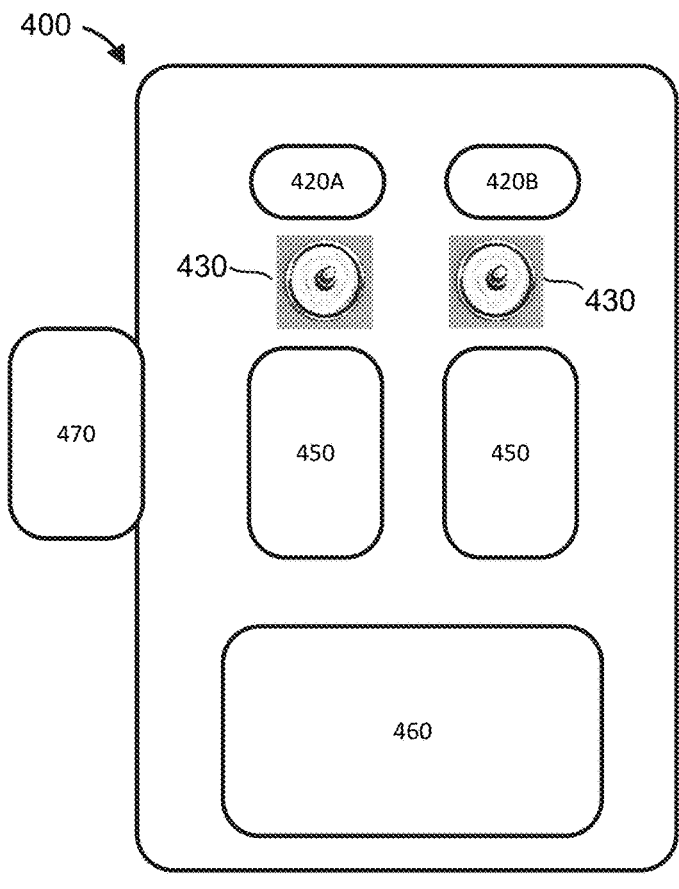
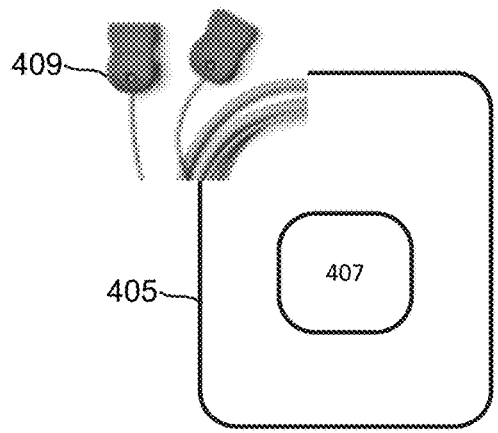
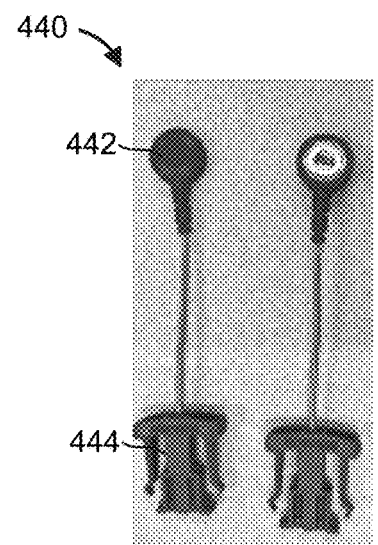
FIG. 10A
FIG. 11

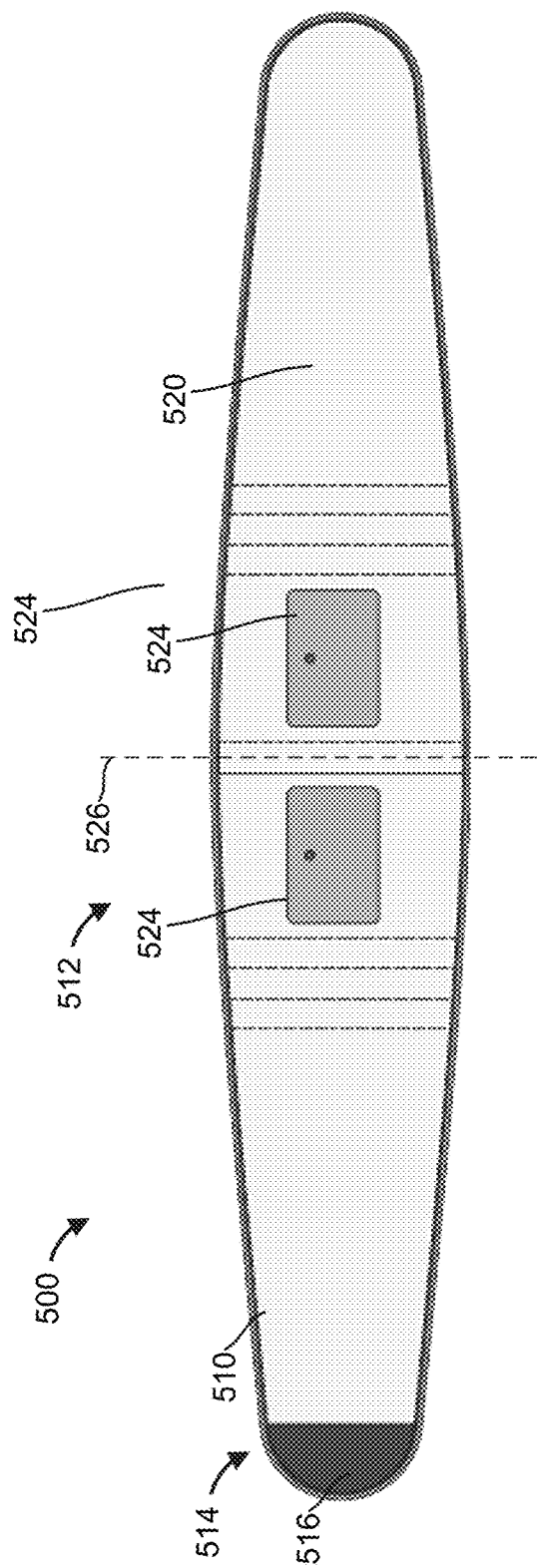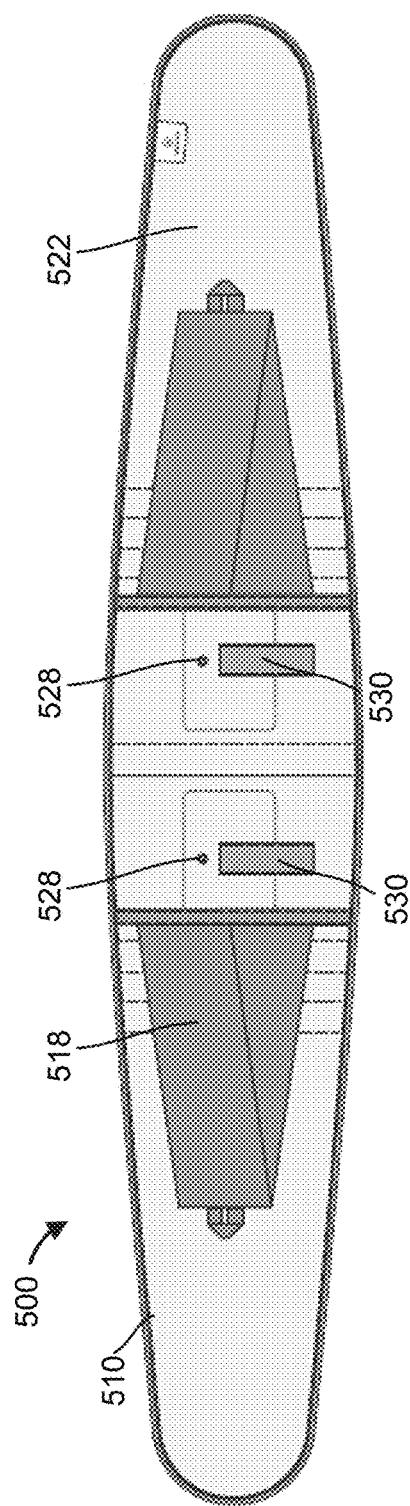
FIG. 12A
FIG. 12B

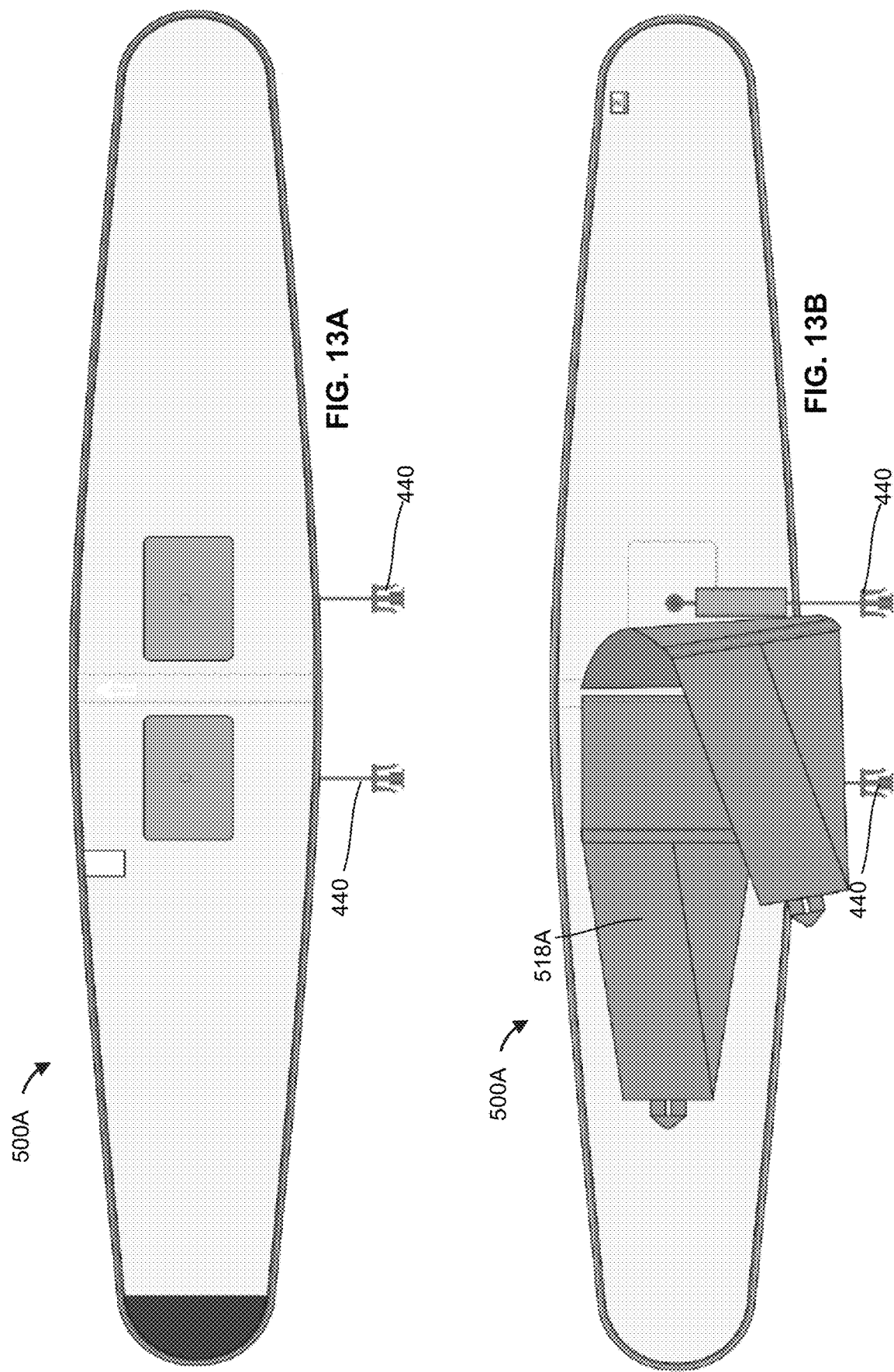

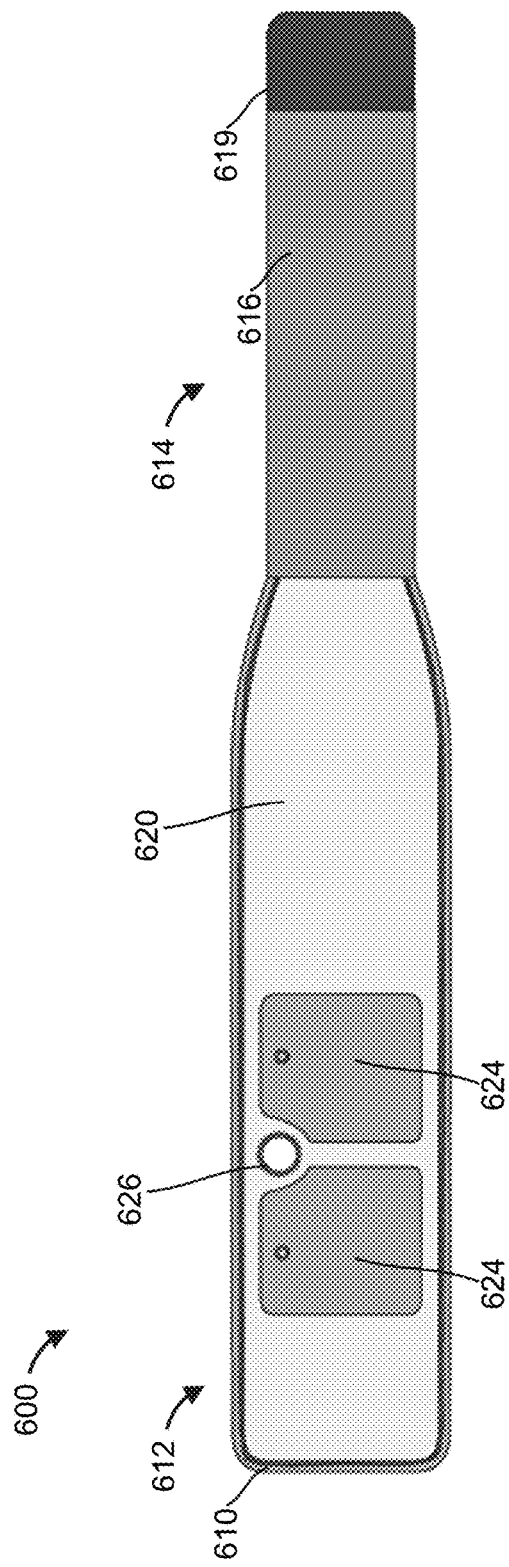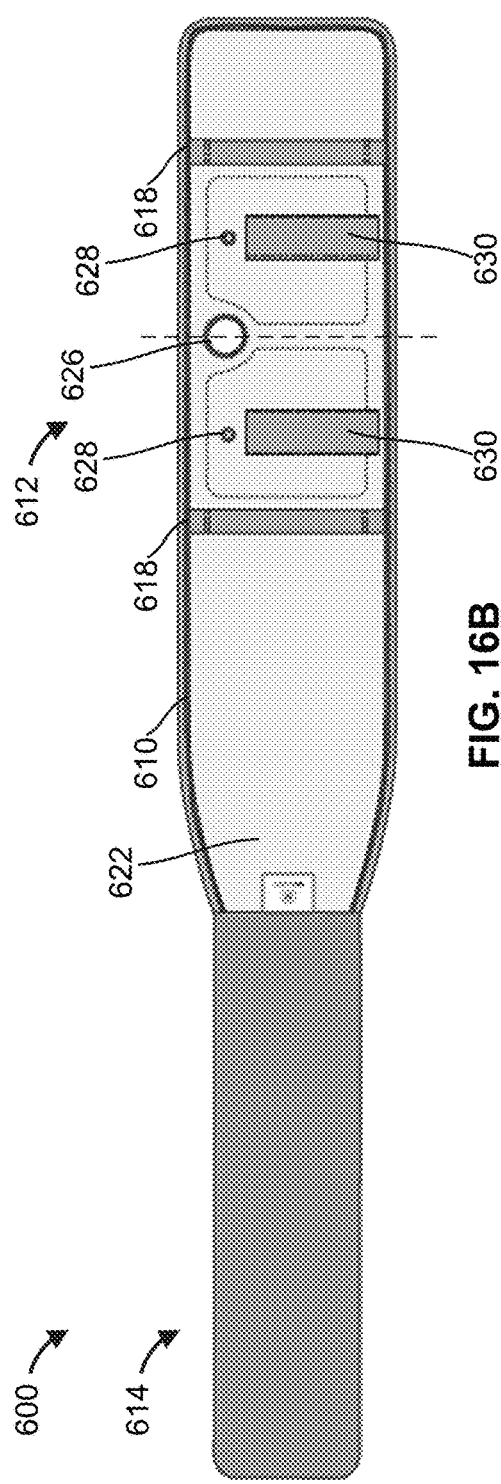
FIG. 16A
FIG. 16B

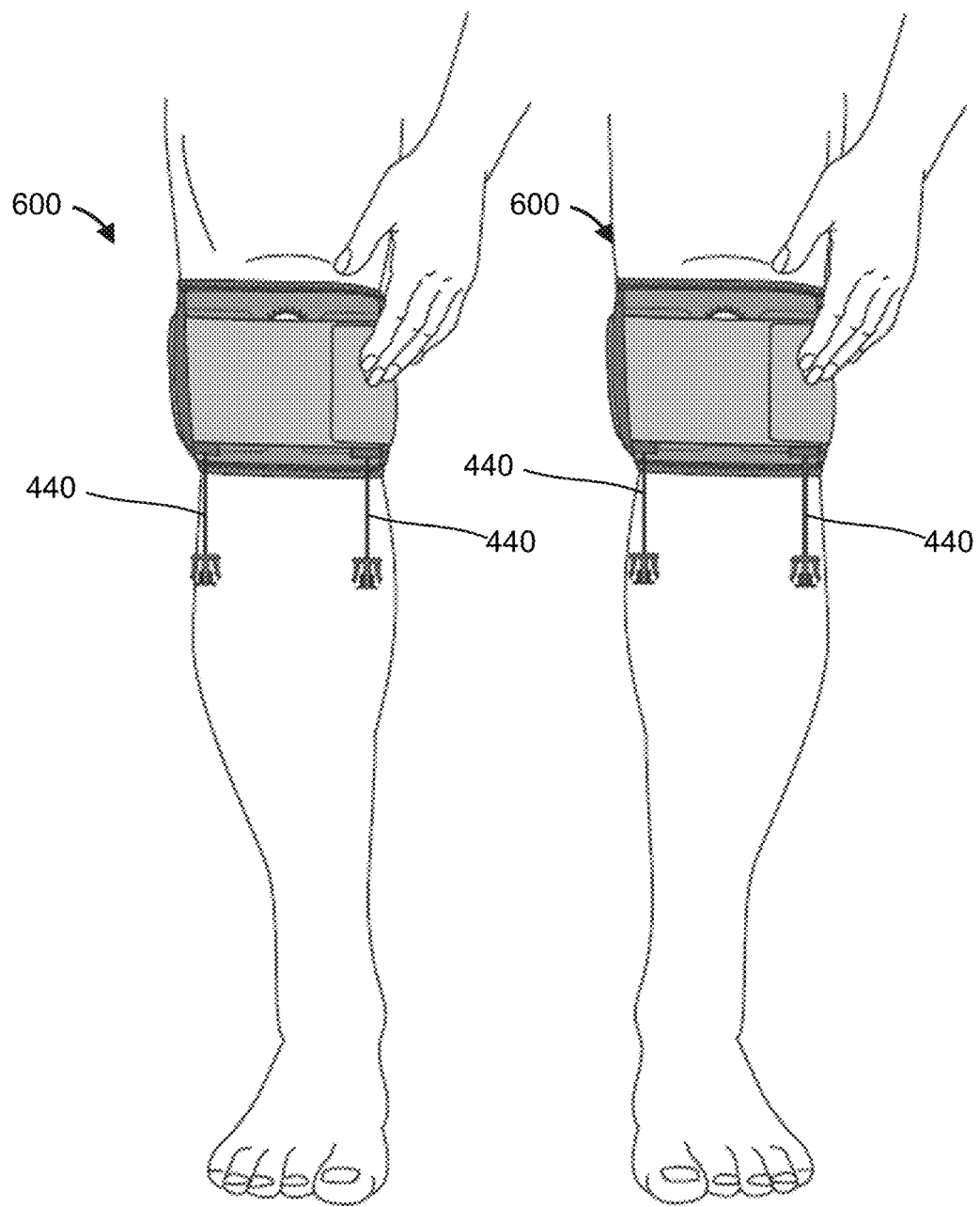
FIG. 16C  FIG. 16D

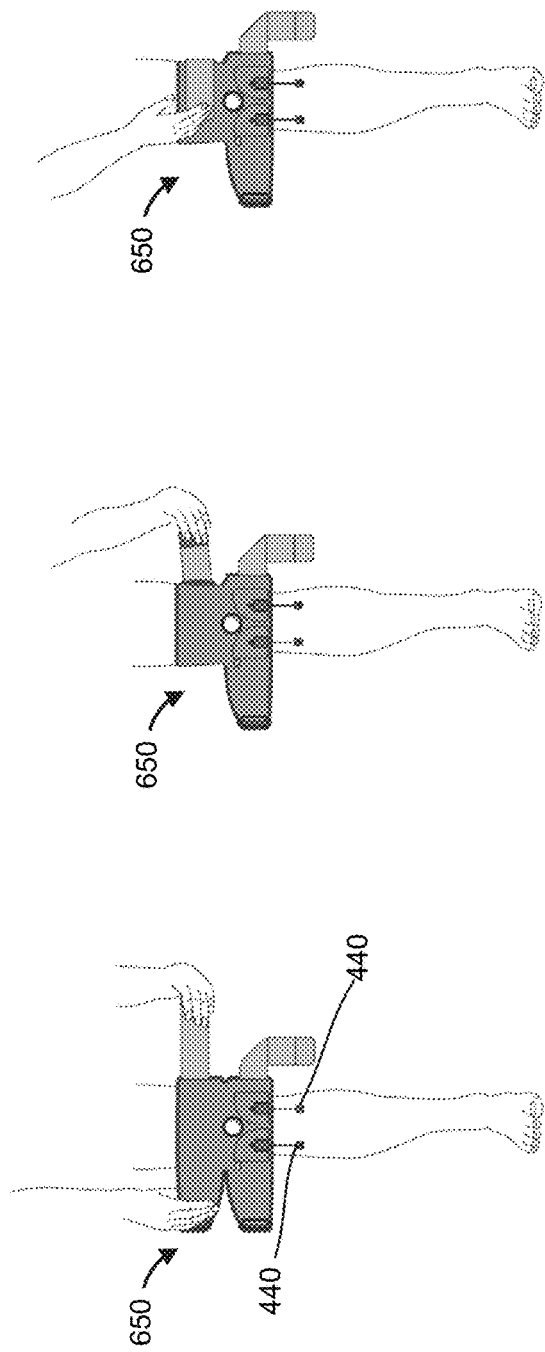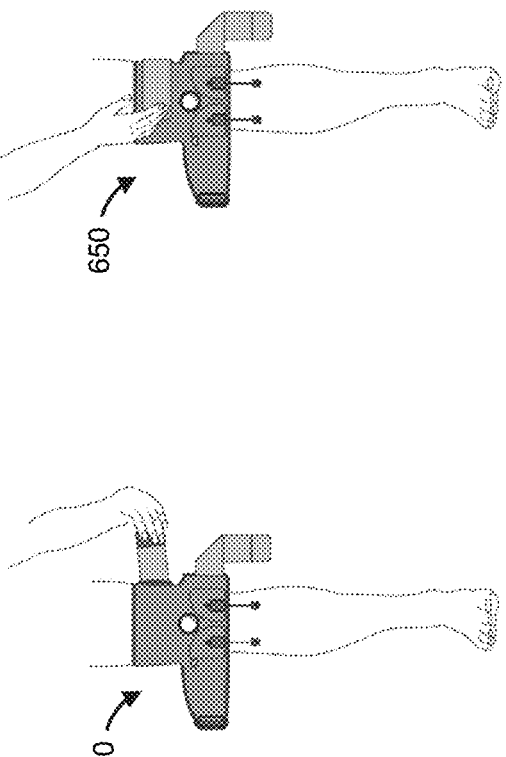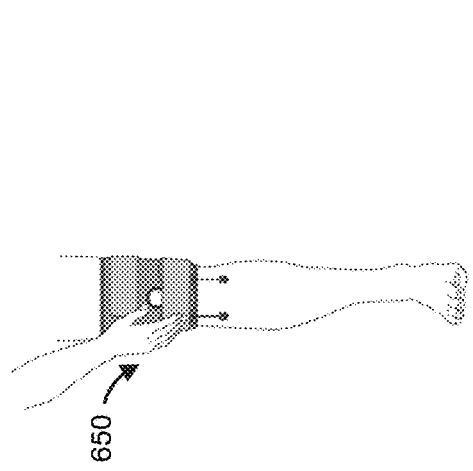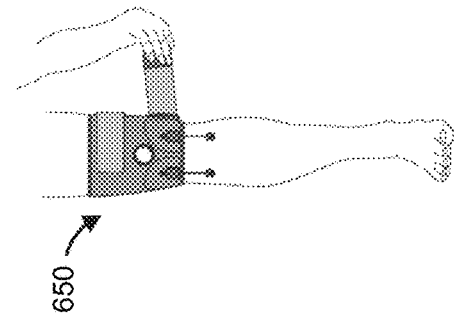
FIG. 19A  FIG. 19B  FIG. 19C  FIG. 19D  FIG. 19E

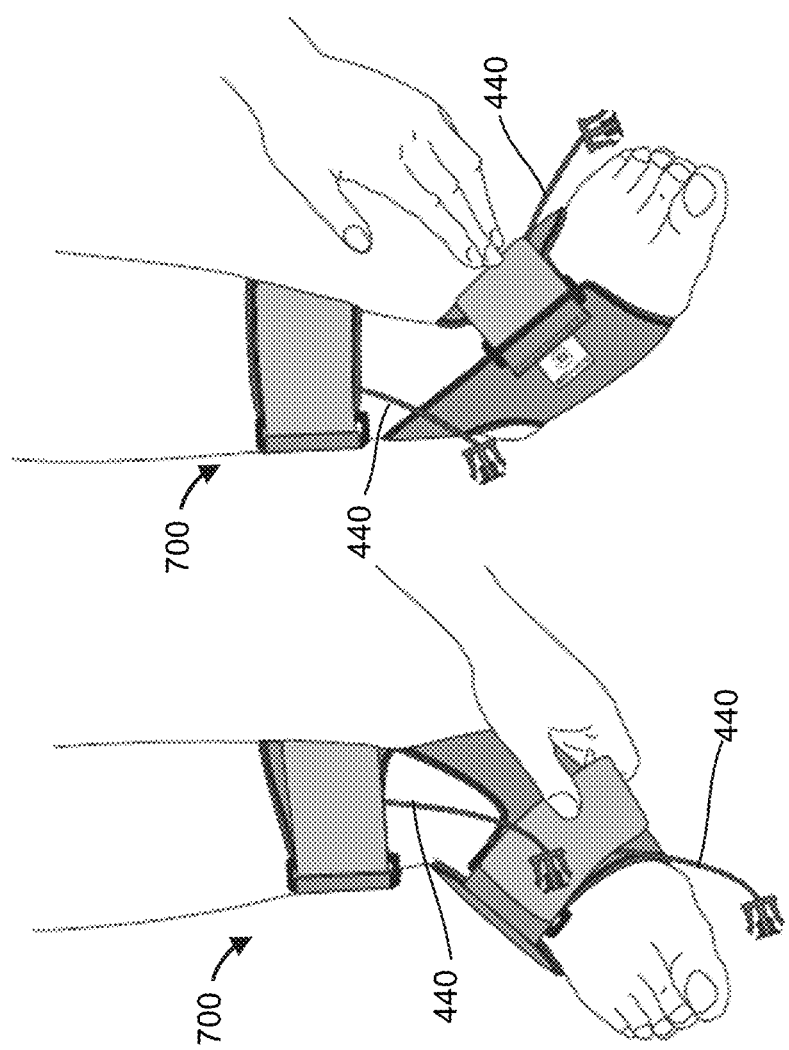

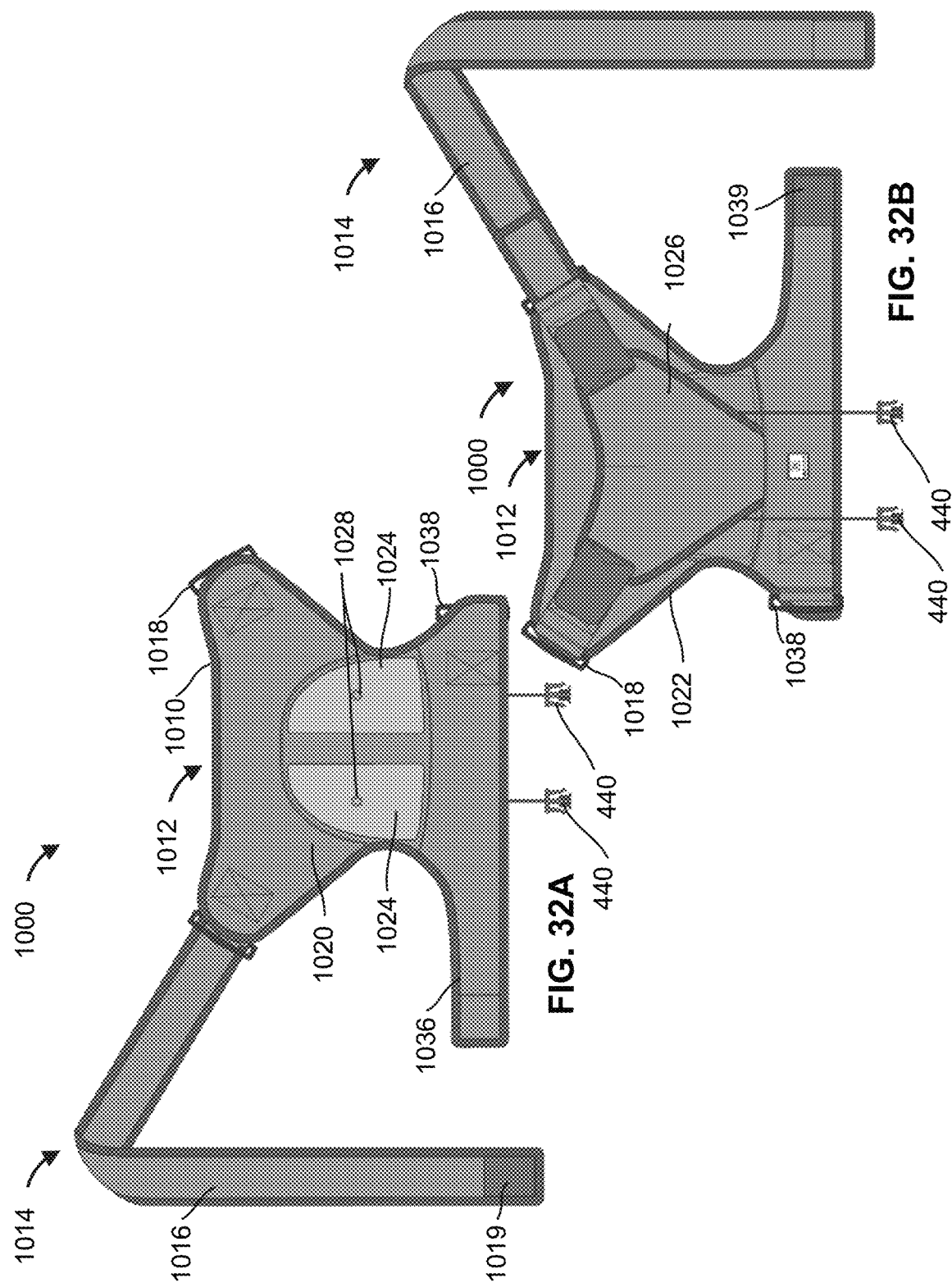

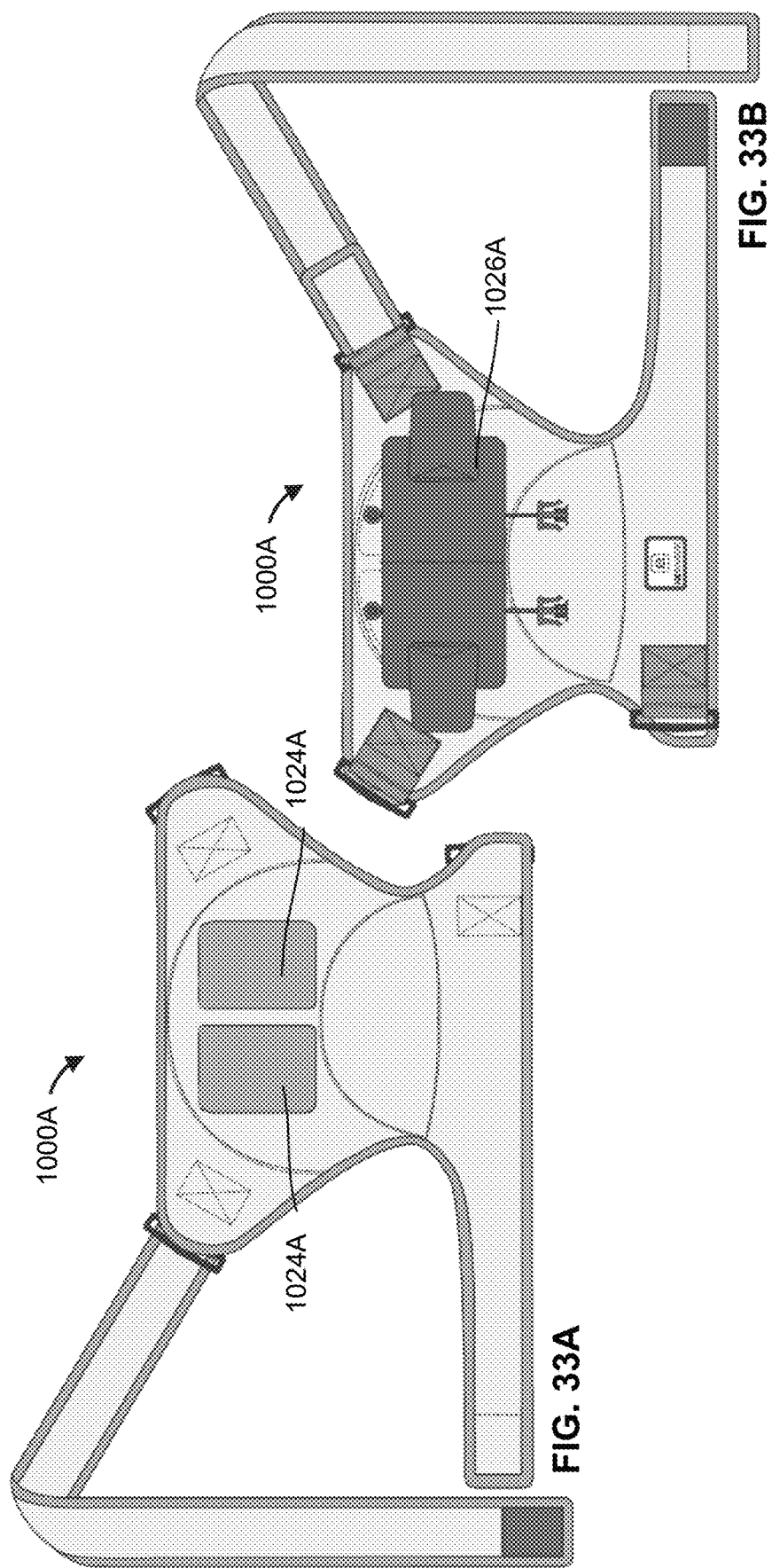

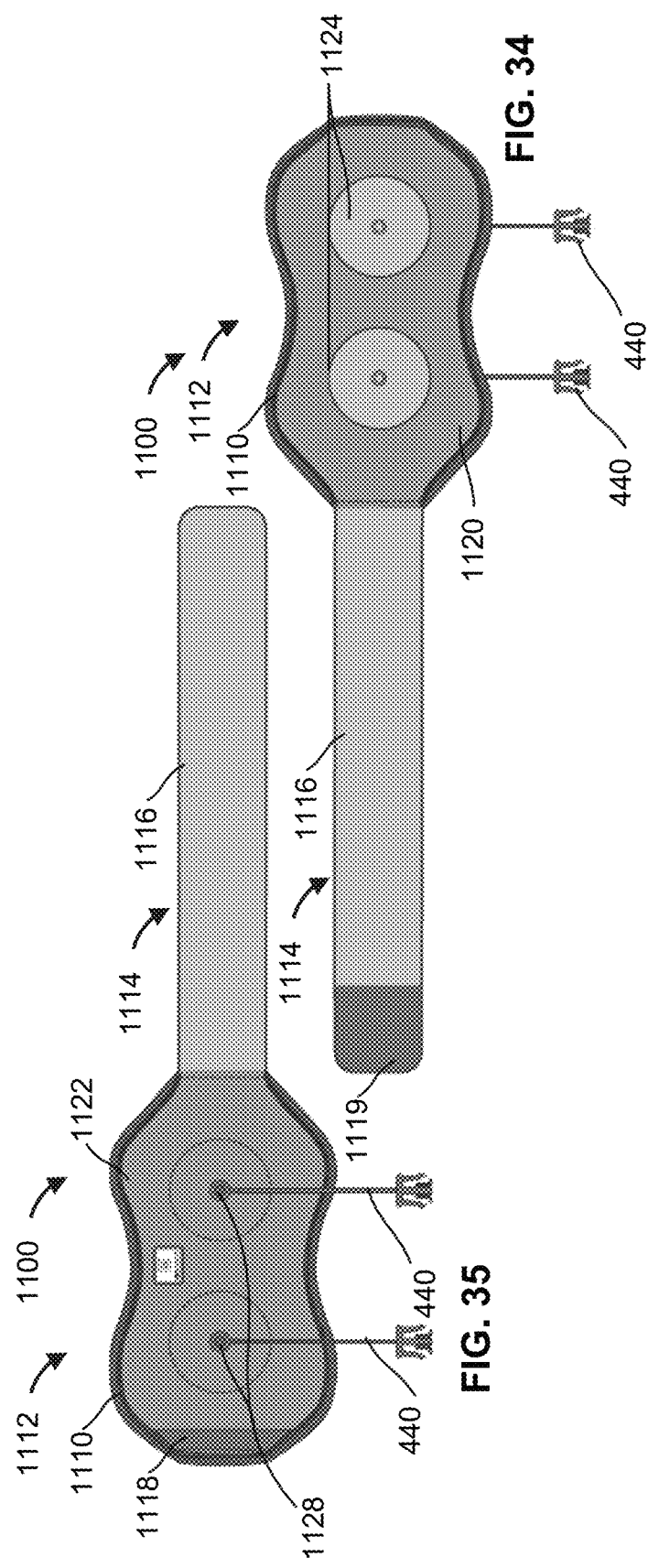

WEARABLE SYSTEM FOR AN ELECTROTHERAPY DEVICE

CROSS-REFERENCE TO RELATED APPLICATION

This application is a continuation-in-part of U.S. patent application Ser. No. 16/661,728 filed Oct. 23, 2019 which claims priority to U.S. Provisional Patent Application Ser. No. 62/749,233 filed Oct. 23, 2018, the entirety of which is incorporated herein by reference.

TECHNICAL FIELD

The present disclosure generally relates to the technical field of pain treatment. More particularly, the present disclosure is directed to a garment for providing electrotherapeutic treatment to a localized portion of the body.

BACKGROUND

Traditionally, electrotherapy devices have generated alternating current frequencies using a variety of different methods. For example, Matthews' U.S. Pat. No. 5,269,304 issued on Dec. 14, 1993 discloses an electrotherapy apparatus that includes at least two electrodes adapted to feed oscillating current to selected sites on or beneath the epidermal or mucous surface remote from the treatment site. The Matthews' Patent uses a common return electrode provided at the treatment site that is subjected to the sum of the currents from the two feed electrodes. The feed electrodes may be contact feed electrodes or capacitive feed electrodes. The feed electrodes may operate at different frequencies so that the treatment site is stimulated by the beat frequency. This may be about 80 or 130 Hz, if an anaesthetizing effect is required. Disclosed embodiments provide electrotherapeutic devices and wearable systems adapted to provide signals from the electrotherapeutic device to a user.

SUMMARY

In some embodiments, the present disclosure includes a wearable garment including a flexible material configured to wrap around a portion of a user's body. The flexible material may include an interior surface configured to contact the user's body and an opposite exterior surface. The garment may further include a first electrode positioned at the interior surface and configured to contact a targeted part of the user's body and a second electrode positioned at the interior surface and configured to contact a targeted part of the user's body. The garment may also include a first electrode connector positioned at the exterior surface and operably connected to the first electrode and a second electrode connector positioned at the exterior surface and operably connected to the second electrode. The first and second electrodes are configured to deliver a therapeutic signal from an electrotherapeutic device via the first and second electrode connectors.

In other embodiments, the present disclosure includes a wearable system including a garment. The garment includes a flexible material configured to wrap around a portion of a user's body. The flexible material includes an interior surface configured to contact the user's body and an opposite exterior surface. The garment may also include a first electrode positioned at the interior surface and configured to contact a targeted part of the user's body and a second electrode positioned at the interior surface and configured to contact a targeted part of the user's body. The garment may further include a first electrode connector positioned at the exterior surface and operably connected to the first electrode, and a second electrode connector positioned at the exterior surface and operably connected to the second electrode. The wearable system may also include an electrotherapeutic device configured to deliver a therapeutic signal to the first and second electrodes via the first and second electrode connectors.

In other embodiments, the present disclosure includes a method for providing therapeutic electric current to a treatment site of a patient. The method includes providing a flexible garment comprising a first electrode and a second electrode, providing an electrotherapeutic device operably connected to the first electrode and the second electrode, positioning the flexible garment with respect to a user's body such that the first electrode and the second electrode are each in contact with a targeted part of the user's body, forming a therapeutic signal configured to reduce pain at a treatment site by simultaneously sending a first signal from the first electrode to the second electrode and sending a second signal from the second electrode to the first electrode, and then simultaneously sending the first signal from the second electrode back to the first electrode and the second signal from the first electrode back to the second electrode.

BRIEF DESCRIPTION OF DRAWINGS

Various aspects of the present disclosure will be or become apparent to one with skill in the art by reference to the following detailed description when considered in connection with the accompanying exemplary non-limiting embodiments.

FIG. 10A is a block diagram of a wearable system for applying an electrotherapeutic signal to a user in accordance with some embodiments of the present disclosure.

FIG. 11 illustrates an embodiment of a wire that may be used in conjunction with the wearable system of FIG. 10 in accordance with some embodiments of the present disclosure.

FIG. 12A is an inside view of a lower back wearable system in accordance with some embodiments of the present disclosure.

FIG. 12B is an outside view of the lower back wearable system in accordance with some embodiments of the present disclosure.

FIG. 13A is an inside view of a lower back wearable system in accordance with some embodiments of the present disclosure.

FIG. 13B is an outside view of the lower back wearable system in accordance with some embodiments of the present disclosure.

FIG. 16A is an inside view of a knee wearable system in accordance with some embodiments of the present disclosure.

FIG. 16B is an outside view of the knee wearable system in accordance with some embodiments of the present disclosure.

FIG. 16C is a depiction of the knee wearable system on a right leg of a user in accordance with some embodiments of the present disclosure.

FIG. 16D is a depiction of the knee wearable system on a left leg of a user in accordance with some embodiments of the present disclosure.

FIG. 19A-19E are a depiction of the knee wearable system on a left leg of a user in accordance with some embodiments of the present disclosure.

FIG. 22 is a depiction of the ankle/foot wearable system on a right leg of a user in accordance with some embodiments of the present disclosure.

FIG. 23 is a depiction of the ankle/foot wearable system on a left leg of a user in accordance with some embodiments of the present disclosure.

FIG. 32A is an inside view of a shoulder wearable system in accordance with some embodiments of the present disclosure.

FIG. 32B is an outside view of the shoulder wearable system in accordance with some embodiments of the present disclosure.

FIG. 33A is an inside view of a shoulder wearable system in accordance with some embodiments of the present disclosure.

FIG. 33B is an outside view of the shoulder wearable system in accordance with some embodiments of the present disclosure.

FIG. 34 is an inside view of a head/neck wearable system in accordance with some embodiments of the present disclosure.

FIG. 35 is an outside view of the head/neck wearable system in accordance with some embodiments of the present disclosure.

DETAILED DESCRIPTION

Figure 1:
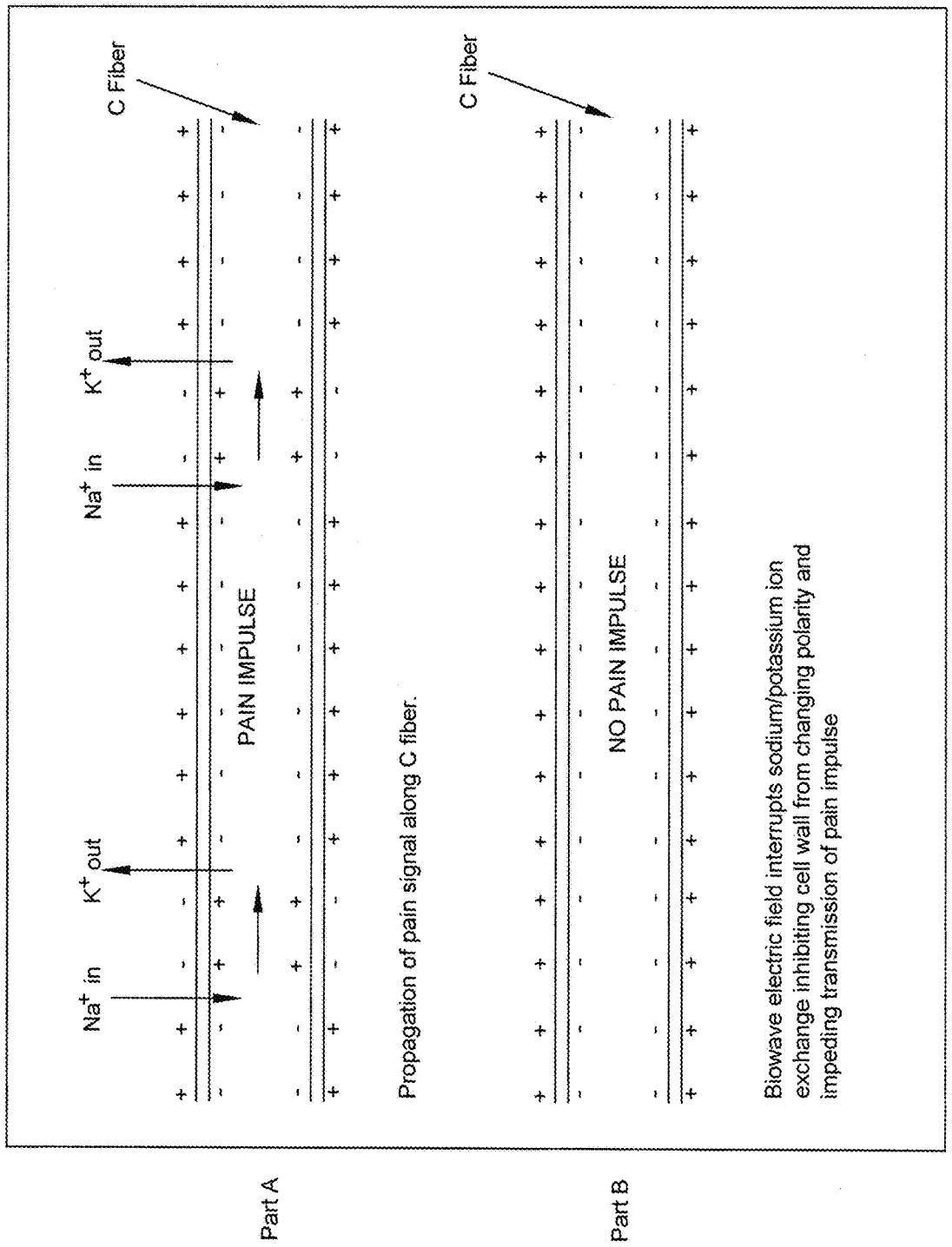
FIG. 1 illustrates the hyperpolarization mechanism of pain reduction in accordance with some embodiments of the present disclosure.

With reference to the figures, where like elements have been given like numerical designations to facilitate an understanding of the drawings, various embodiments of an apparatus for a multi-purpose handheld tool are described. The figures are not drawn to scale The following description is provided as an enabling teaching of a representative set of examples. Many changes can be made to the embodiments described herein while still obtaining beneficial results. Some of the desired benefits discussed below can be obtained by selecting some of the features discussed herein without utilizing other features. Accordingly, many modifications and adaptations, as well as subsets of the features described herein are possible and can even be desirable in certain circumstances. Thus, the following description is provided as illustrative and is not limiting.

This description of illustrative embodiments is intended to be read in connection with the accompanying drawings, which are to be considered part of the entire written description. The drawing figures are not necessarily to scale and certain features of the invention can be shown exaggerated in scale or in somewhat schematic form in the interest of clarity and conciseness. In the description of embodiments disclosed herein, any reference to direction or orientation is merely intended for convenience of description and is not intended in any way to limit the scope of the present disclosure. Relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" "interconnected," "attached," and "affixed," refer to a relationship wherein structures are secured or attached to one another either directly or indirectly through intervening structures, as well as both movable or rigid attachments or relationships, unless expressly described otherwise. The terms "operatively connected" or operatively coupled" are such an attachment, coupling or connection that allows the pertinent structures to operate as intended by virtue of that relationship. The term "adjacent" as used herein to describe the relationship between structures/components includes both direct contact between the respective structures/components referenced and the presence of other intervening structures/components between respective structures/components.

As used herein, use of a singular article such as "a," "an" and "the" is not intended to exclude pluralities of the article's object unless the context clearly and unambiguously dictates otherwise.

In various embodiments, a differentially-applied frequency-separated electrotherapy apparatus and method is disclosed for providing therapeutic electric current to a treatment site of a patient. The apparatus and method include having at least two individually generated and amplified oscillating or pulsing alternating currents, of frequencies which differ from each other by as a little as 1 Hz and up to about 300 Hz, wherein the base frequency value of the two frequencies can be between 200 Hz and 500 KHz. The apparatus and method require at least two electrodes adapted to act as pain site and return electrodes which provide electric current beneath the epidermal or mucous surface of the patient, directly over the source of pain.

In some embodiments, the method of electrotherapy includes providing two individually generated and amplified signals with a frequency difference between them which is applied to one or more pairs of electrodes placed on the body directly over locations of pain and/or over the origin of the pain. According to various embodiments, as will be described in further detail below, since the signals share a common power supply return path, each signal's electrode acts as the return path for the opposing signal. Advantageously, the signals non-linearly mix on polarizable weakly rectifying structures along the current path to evoke a neuro-stimulated pain signal transmission blocking effect by interfering with nerve impulse signal transmission.

In various embodiments, at least one pair of electrodes are placed directly over locations of pain, on or beneath the epidermal or muscular surface of a patient coupled to a generator feeding via the at least one pair of electrodes with two or more oscillating or complex morphology electric currents to a patient. In some embodiments, the respective selected electrode placement locations are opposite one another on the patient's body with a pain site located on a line vector in between the electrodes with the line vector perpendicular to each skin surface on which the electrodes reside. In various embodiments, as described below, the at least one pair of electrodes may be placed directly over a single location of pain. In some embodiments, the currents generated by the at least one pair of electrodes are a frequency of at least about 1 KHz and have a current difference between each electrode respectively as little as 1 Hz by up to about 300 Hz. As described in part above, a non-linear action of nerve fiber membranes causes a multiplication of the two independent high frequency signals in a volume of tissue surrounding and beneath each of the at least two electrodes to produce a therapeutic effect in the hemisphere surrounding and beneath each of the at least two electrodes. The multiplication yields a distribution of synthesized sum and difference frequencies among which is a therapeutic low frequency signal that is equivalent to a beat frequency of the signals.

A described in part above, two high frequency electronic wave-forms are introduced into the body non-invasively through at least one pair of disposable electrodes placed on the skin directly over the pain site, according to some embodiments. In various embodiments, for two locations of pain, each electrode is placed directly over a painful area. In some embodiments, for one location of pain, one electrode is placed directly over a single location of pain, the second electrode may be placed over a bony area which is a comfortable location to receive stimulation.

The Feed Signals are exponentially multiplied by materials within the body giving rise to a low frequency component, the beat frequency, in the form of an electric field within the volume of tissue the shape of a hemisphere beneath as well as surrounding the electrode, the size of which is defined by the geometry of the electrode. The size and shape of the volume of tissue affected can be changed and is dependent upon electrode placement, geometry and materials, as well as the amplitude of the Feed Signals.

The disclosed embodiments further apply to an electrode garment that may be placed and held against a selected body part. The disclosed garments may be designed as part of a neurostimulation system to provide relief of chronic, acute or post-operative pain. The size and location of each electrode is designed and optimized to deliver a summed high frequency alternating current neurostimulation into deep tissue in the body. Such garments cannot be used with conventional TENS devices.

In the disclosed embodiments, electrode size and location depend upon the part of the body being treated. In some embodiments electrode sizes might range from 4"×5" on the lower back to 3"×3.5" for the knee to 1.5"×8" electrodes that can encompass the wrist and hand or foot and ankle. Electrodes are designed to be located over common body locations where pain presents. Electrode sizes are configured to accommodate the magnitude of intensity that can be tolerated by a patient. Patients can typically increase the output of a BioWave neurostimulator to higher voltages (22-25V) on knees, ankle and feet, mid range voltages (13-15V) on back and shoulders and lower range voltages (8-13V) on elbow, wrist, hand and neck treatments.

Physiological Application

FIG. 1 illustrates the hyperpolarization mechanism of pain reduction according to various embodiments. Pain signals from receptors that are large enough to exceed the trigger threshold for the exchange of sodium and potassium ions across a nerve cell membrane do so through changes in the ion permeability of this membrane. This ion exchange causes a polarity change across and along the cell wall of the nerve fiber affecting the transmission of pain information along certain C type fibers as shown in Part A of FIG. 1. Several mechanisms of action caused by the Beat Frequency to reduce pain, namely (1) Frequency Conduction Block (also called Hyperpolarization), (2) Gate Control, (3) increased blood flow and (4) the release of endorphins or other opiate-like analogs.

Frequency Conduction Block. In Part B of FIG. 1, with the low frequency electric field in place, the membranes of C fibers that fall within the electric field are hyperpolarized. As a result, the sodium/potassium ion exchange is inhibited and the cell wall is prevented from changing polarity (from a negative potential to a positive potential) thus impeding the transmission of action potentials. As a result, pain impulses along the C fibers are blocked—similar in action to local chemical anesthesia, except without any deleterious side effects.

A further explanation of the therapeutic Hyperpolarization mechanism is that the resulting beat frequency, its signal morphology and current densities within the volume of tissue around and below each electrode, causes an alteration in the nerve cell membrane's sodium/potassium ion concentrations or ion exchange kinetics. As a result, the charge polarity of the nerve cell wall is prevented from changing and is therefore unable to transmit pain impulses.

Empirically, the difference signal does affect the sensory fibers, as some loss of proprioception at the skin as well as induction of hypoesthesia in the region of the active low frequency electrical field occurs about 5 minutes into the treatment, similarly to but not as absolute as a chemical anesthetic. Following a 30-minute treatment, hypoesthesia remains typically for up to 20 minutes post treatment.

Empirically, the difference signal also affects muscle tissue, which is polarized, in that it holds muscle tissue in tension during the treatment, which results in the patient feeling a deep, smooth sensation from the electrical field which is comfortable and provides for excellent patient compliance using the device.

Figure 2:
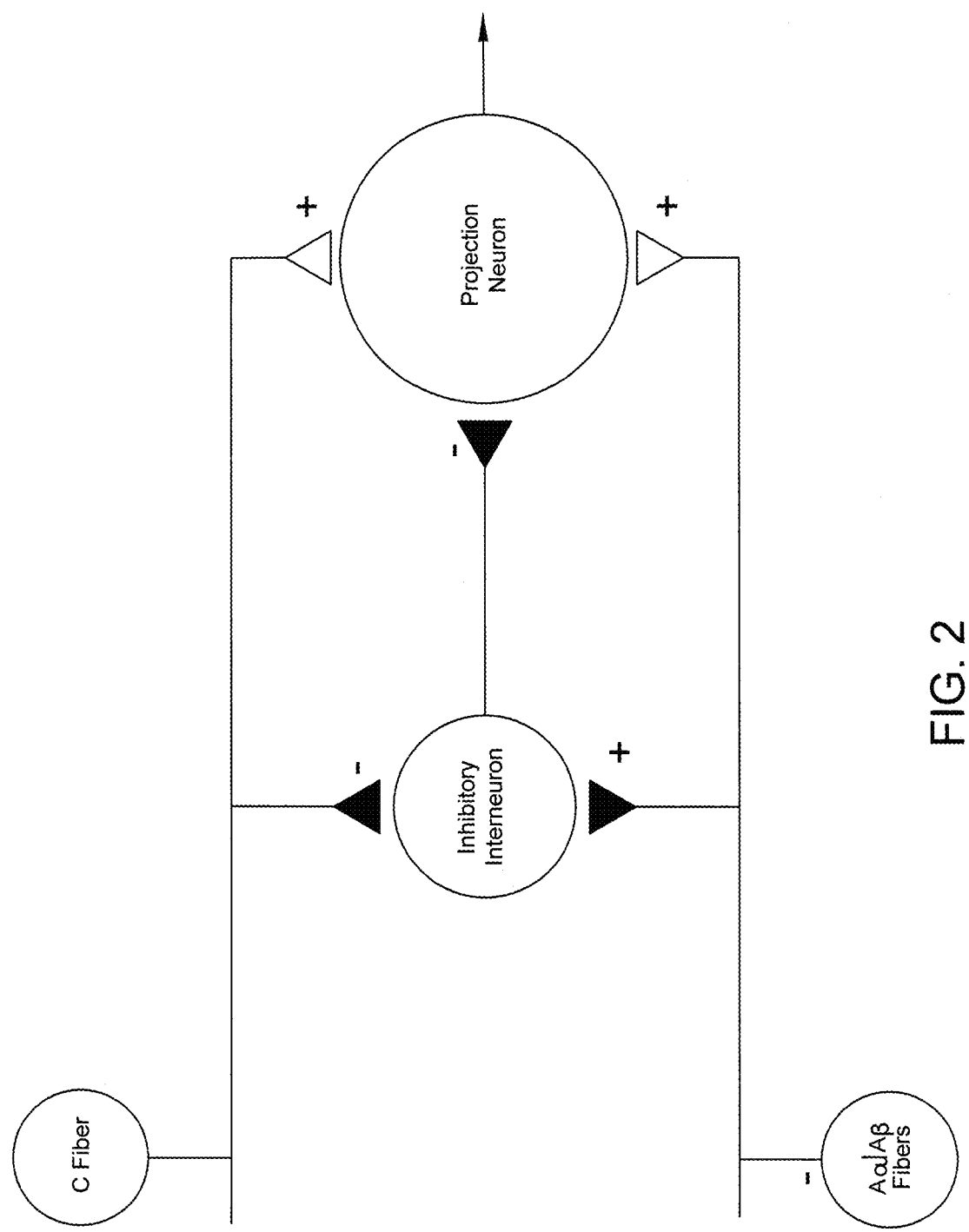
FIG. 2 illustrates the gate control mechanism of pain reduction in accordance with some embodiments of the present disclosure.

Gate Control. Gate Control focuses on interactions of four classes of neurons in the dorsal horn of the spinal cord as shown in FIG. 2: (1) C fibers which are unmyelinated, (2) Aβ/Aδ fibers which are myelinated, (3) projection neurons whose activity results in the transmission of pain information, and (4) inhibitory interneurons which inhibit the projection neuron, thus reducing the transmission of pain information.

The projection neuron is directly activated by both Aβ/Aδ and C fibers. However, only the Aβ/Aδ fibers activate the inhibitory interneuron. Thus, when Aβ/Aδ fibers are stimulated by the beat frequency from the electric field, the inhibitory interneuron is activated and prevents the projection neuron from transmitting pain information to the brain. The C fiber is left in a state analogous to an open electrical circuit so that transmission of the sensation of pain is suppressed.

Increased Blood Flow. An additional mechanism of action is that the resulting low frequency electrical field that forms beneath and surrounding both electrodes can accelerate any charged species under its influence. This may lead to an increase in local blood flow. Medical studies have shown that proper blood flow is required for the healing of any wound or injury. With the treatment application of the apparatus, there appears to be a concomitant increase in blood flow in the volume of tissue where the electric field is present that accelerates healing. Clinical evidence shows there is also a concomitant increase in range of motion and reduction of stiffness for up to 24 hours following the treatment.

Release of Endorphins or Other Opiate-like Analogs. Empirical evidence suggests that residual pain relief and an increase in range of motion can last for up to 24 hours following a thirty (30) minute treatment. The residual effect involves either a refractory mechanism involving the membrane itself or the local release of endorphins, enkaphlins or other opiate-like analogs.

Unique Control and Management Apparatus and Method

According to various embodiments of the present disclosure, the electro therapy device controls the output of a handheld high frequency neurostimulator for providing a therapeutic treatment inside the body to treat pain and other conditions by utilizing a digital amplifier, feedback control utilizing filters, and other circuitry to provide comfortable treatment to patients. Advantageously, the electrotherapy device described in the present disclosure eliminates electrical spikes and jolts regardless if the patient is siting or moving about during the treatment.

One embodiment of the electrotherapeutic apparatus involves two signals: S1 represents a first signal at a first frequency and S2 represents a second signal at a second frequency. S1 and S2 are linearly independent AC signals. At any given instant one electrode can act as the source of the signal while the other electrode can serve as its return. Due to the AC nature of the signal these roles become reversed as a function of the instantaneous polarity of said signal. The time dependent roles of the electrode vary for the two signals as they are not in phase. It will be appreciated that the effect within the body from the combination of S1 and S2 passing through the body to the respective electrodes produces the pain-relieving effects described above.

Figure 3:
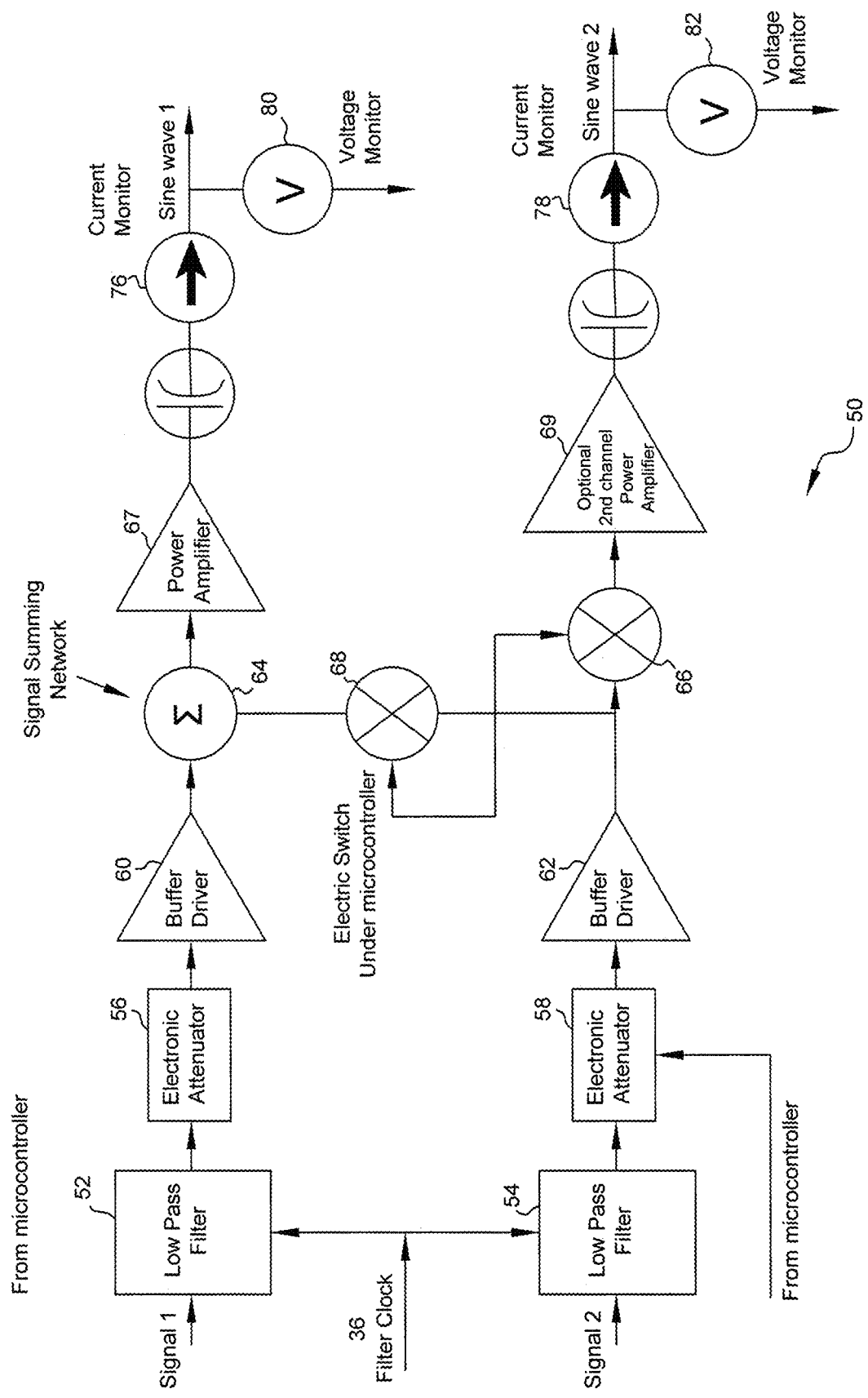
FIG. 3 illustrates output portions of an electrotherapeutic device in accordance with some embodiments of the present disclosure.

FIG. 3 illustrates output portions of an electrotherapeutic device in accordance with some embodiments of the present disclosure. More specifically, FIG. 3 depicts a sub-system 50 for converting Signal 1 and Signal 2 to sine wave signals. As discussed above, the ultimate output signals of the electrotherapy device need to be as close to a pure sine wave as possible. Signal 1 and Signal 2 are initially logic level square-type waves. These signals are limited to 0.6V amplitude by the transistor limiters. The outputs of these limiters are applied independently to high-order low pass filters 52 and 54. The filter clock 36, if switched capacitor filters are used, output is coupled to each of the filters. These filters suppress the higher order harmonics present in the limited square waves leaving low distortion sine waves at the reference frequencies. These sinusoidal signals are amplified and applied to electronic attenuators or programmable amplifiers 56 and 58 (under microprocessor 12 control) to control the level of the signal applied to the power amp stage, discussed below, and ultimately to the patient. The signals are then buffered 60 and 62 and applied to a power gain stage. The power stage consists of one or more amplifiers 67, 69 capable of supplying a wide range of voltages into any physiological and electrode load over the frequency ranges used. Depending on the desired level of system integration and/or portability required, this amplifier stage can be either of the linear Classes A or $AB_1$ or the nonlinear switching Class D type. In various embodiments, use of the Class D amplifier, as discussed in further detail below, provides the efficiency and in turn, minimal heat generation properties, to allow enclosure of the therapeutic device for water resistant properties.

For Class D amplifiers a high-speed comparator varies the pulse width of a switching power transistor (MOSFET type). This modulation is called pulse width modulation and is driven by the original signal's frequency, amplitude and desired gain. The sampling of the reference signal, derived from either a PLL reference or DDS, is sampled at a rate at several orders of magnitude higher than the highest frequency component in said reference. The output of the power transistor is low-pass filtered by a passive LC network to yield the amplified signal. The mode of amplifier operation is particularly attractive since power conversion efficiencies of over 90% can be obtained as opposed to the efficiencies of linear amplifiers which are between 40% to 70%. The microcontroller 12 sets, via electronic switching 68, whether the signals are summed at an amplifier to create the mixed signal or applied individually to the power stage and thereby allows the mixing to take place within the patient's body. Additionally, one or more channels and/or return signal paths can be multiplexed with electronic power switching during zero crossing of the sine wave signals (via processor control). This multiplexing or switching allows multiple electrodes to be fed from the amplifiers or connected to an analog return. This is done to synthesize a larger effective target region on or within the patient. The patient is electrically isolated from leakage to power mains by the isolated plastic housing of the Apparatus and by the use of a battery power supply.

Figure 4:
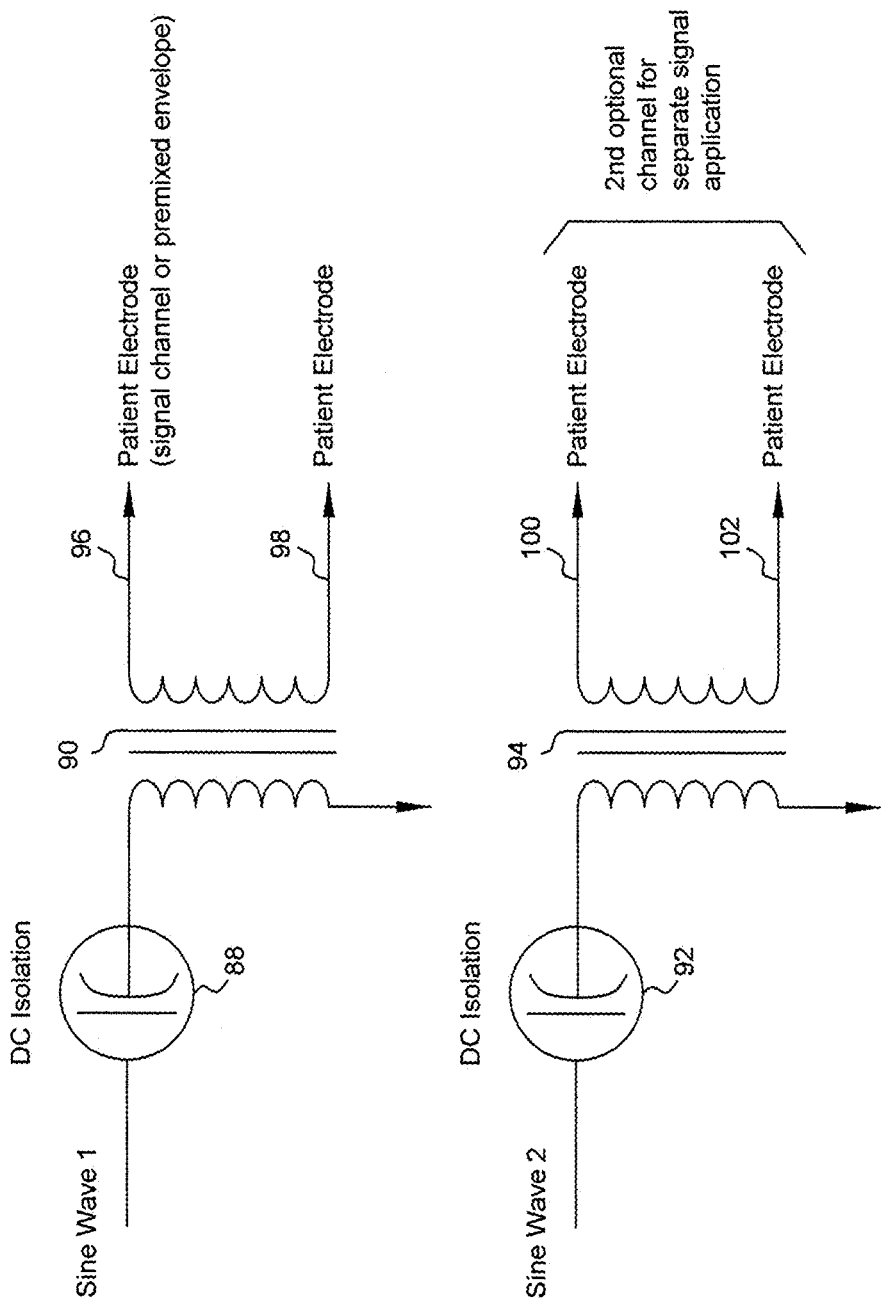
FIG. 4 illustrates the coupling of Sine wave 1 and Sine wave 2 to the electrodes when the apparatus is constructed around ground reference (local Apparatus ground) linear power amplifiers in accordance with some embodiments of the present disclosure.

FIG. 4 illustrates the coupling of Sine wave 1 and Sine wave 2 to the electrodes when the apparatus is constructed using around ground referenced (local Apparatus ground) linear power amplifiers in accordance with some embodiments of the present disclosure. The sine wave signal is coupled from the junction of current monitor 76 or 78 and voltage monitor 80 or 82 or 82 to a DC isolation capacitor 88 or 92. This capacitor removes any remaining DC component on the sine wave signal. The sine wave signal is coupled to transformer 90 or 94. The output of the transformer 90 is coupled to the patient electrodes. One output of each transformer 96 or 100 is coupled to a large signal electrode and the other to a small return electrode 98 or 102. The transformer provides voltage gain and patient/apparatus isolation. With bridged amplifiers or in Class D operation no such transformers are required unless additional voltage gain is needed. In various embodiments, the Dispersive electrode has a much larger surface area contacting the patient than the Pain Site electrode. This size ratio of the Dispersive electrode to the Pain Site electrode is at least 2:1. In some embodiments, the electrodes are the same size and act as both pain site and return electrodes for each other depending on the opposing delivery of the signals.

In some embodiments, a feedback network is disclosed. In various embodiments, the feedback network consists of two functional parts: 1) a circuit (Hardware), that monitors the patient-applied current and possibly voltage and 2) software that determines if the values measured require an output level change (Software). The parameter derived from the current and voltage is the impedance across the patient-applied electrodes. This parameter has been found by studies to be essentially invariant at a given frequency (frequency interval for this device) and over the range of applied potentials used clinically. Further, any impedance change due to a change in patient position essentially disappears when he or she either returns to the position held before the impedance change or after there is an equilibration of blood flow.

Figure 5:
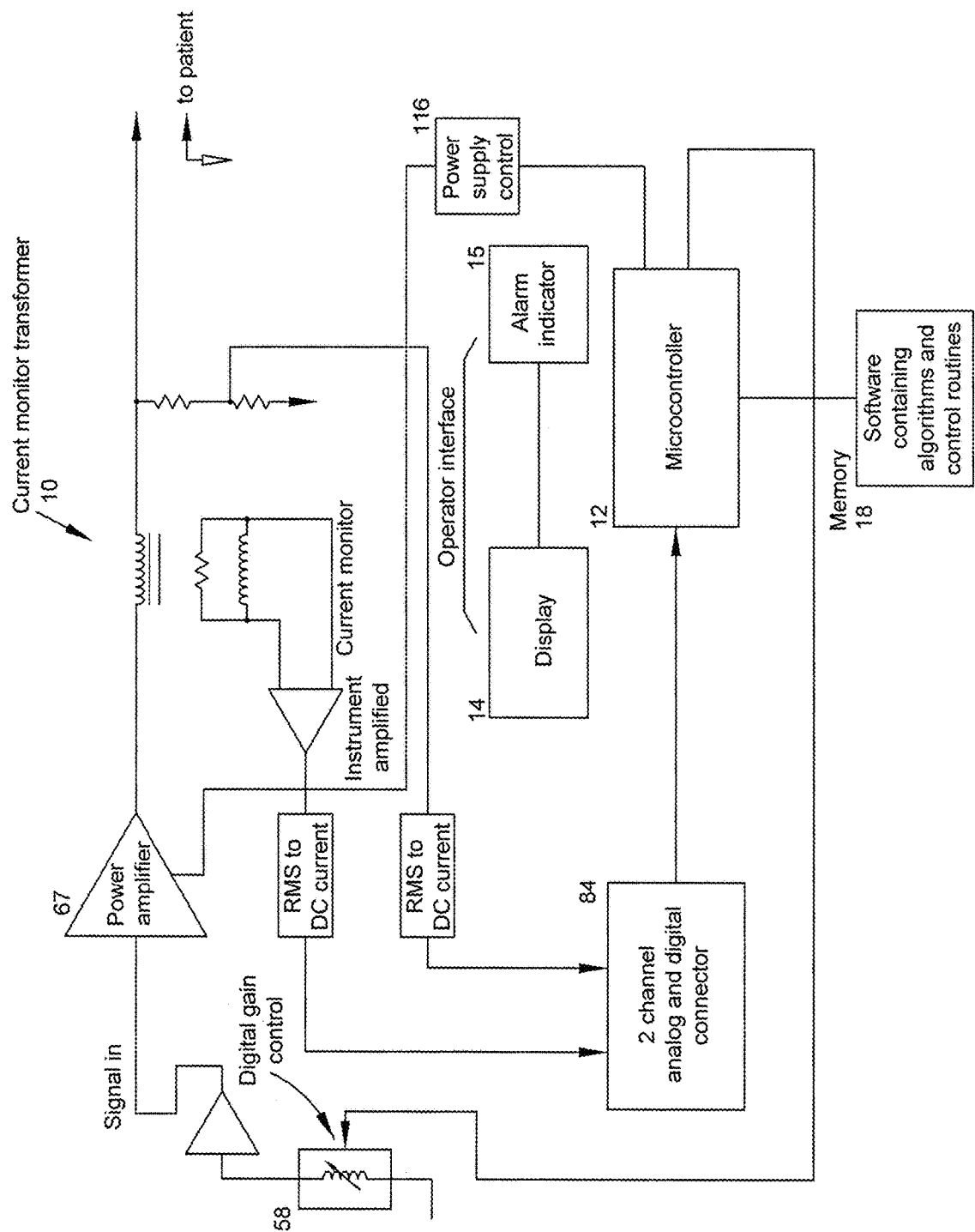
FIG. 5 illustrates the structure of an electrotherapeutic apparatus in accordance with some embodiments of the present disclosure.

FIG. 5 illustrates the structure of an electrotherapeutic apparatus according to some embodiments of the present disclosure. In various embodiments, a microcontroller 12 supervises the entire operation of the apparatus. The microcontroller 12 is responsible for interpreting operator commands and for displaying system status on the display panel 14. Additionally, the processor controls the frequencies of the signal sources, their levels and compensates for any variation in system load. This last function is important since changes in patient electric load can affect the signal level and the perceived sensation of the apparatus effect. The microcontroller 12 uses feedback to control signal levels by comparing the immediate electrical load to previously "learned" characteristic rules for a particular patient. The microcontroller 12 provides input to the digital gain control unit 58. Additionally, the microcontroller 12 receives operation instructions from software containing algorithms and control routines stored in memory 18. In various embodiments, memory 18 may be pre-programmed by an operator. The microcontroller 12 provides instructions to various portions of the signal generation system. The signal system generates two signals. In some embodiments, microcontroller 12 is also responsible for displaying alarms and indications via an indicator unit 15. In some embodiments, this includes an LED display unit having different colors. By way of example, the indicator unit 15 may display Green for indicating battery strength or charge level of the portable unit. Other parameters may identify Bluetooth capability, signal intensity, treatment time, and/or indicate errors or aid in troubleshooting. One of ordinary skill in the art will appreciate that the indicator unit 15 may display various visual indicators useful to a patient for displaying alarms and operations of the electrotherapeutic unit.

The microcontroller supervises the operation by adjusting the digital gain control 58 for the apparatus. As described above, the signals from above are buffered 60 and 62 and applied to a power gain stage. The power stage consists of one or more amplifiers 67, 69 capable of supplying a wide range of voltages into any physiological and electrode load over the frequency ranges used. The second class of amplifiers, which also improves performance in a portable system, is that of Class-D.

As described above, there are several ways of generating and amplifying signals. All methods rely on individual oscillators and amplifiers. Class $AB_1$ amplification is a well-known method for amplifying sinusoidal signals. In the present disclosure the input to these amplifiers are controlled-amplitude sinusoidal signals of differing frequencies. Regulation of the output signal, as a function of load impedance, is achieved by the close-looped feedback network which also can either alter the gain of the power amplifier or the amplitude of the power amplifier's input signal.

Another method uses Class D switching amplifiers. There are two ways these amplifiers can be used to generate the signals. In one method pulse width modulated signals, representing the two frequencies is generated by a microcontroller 12. The width of the pulses defines the amplitude of the final signals and the rate of the pulse packet defines the frequency. These pulse packets drive a set of field effect switching transistors. The output of these transistors is low-pass filtered, reconstructing the sinusoidal signal of the desired amplitude. The second method uses a comparator, connected to a reference sinusoidal signal of set amplitude and a triangular ramp signal. The output of the comparator is a pulse width modulated signal that drives the same circuit, as mentioned above, to generate the output signal. Regulation of the output signal can be achieved by a feedback loop from the output to a summing circuit at the input or monitoring the output using an analog-to-digital circuit on the system's microcontroller 12. The microcontroller 12 can use the digital values of the changes in the output signal, due to changes in load impedance, to adjust the pulse width modulation signal to compensate for these variations.

The unique third method is one derived from high-efficiency radio frequency amplifiers—Class E. Class E is a switching amplifier where a power MOS field effect transistor is driven by a square wave signal whose repetition rate corresponds to the desired output frequency. The amplified pulse is bandpass-filtered recreating an amplified sinusoidal signal. The amplitude of the signal is set by the power supply voltage level. Regulation of the output is achieved by sampling the output signal and using it to control the power supply voltage level to maintain fixed output signal amplitude independent of load impedance. The regulation circuit can be realized by direct hardware feedback or by using the microcontroller's 12 analog-to-digital converter to measure the output amplitude and using the difference between desired amplitude and actual amplitude to set the control voltage on the power supply.

Advantageously, the ability to regulate the output of a digital amplifier into a dynamic load makes for a much more comfortable smooth treatment sensation as the patient moves during treatment. This ultimately results in excellent patient compliance using the device. Regulation of the output signal can be achieved by a feedback loop from the output to a summing circuit at the input or monitoring the output using an analog-to-digital circuit on the system's microcontroller. The microcontroller can use the digital values of the changes in the output signal, due to changes in load impedance, to adjust the pulse width modulation signal to compensate for these variations.

Figure 6:
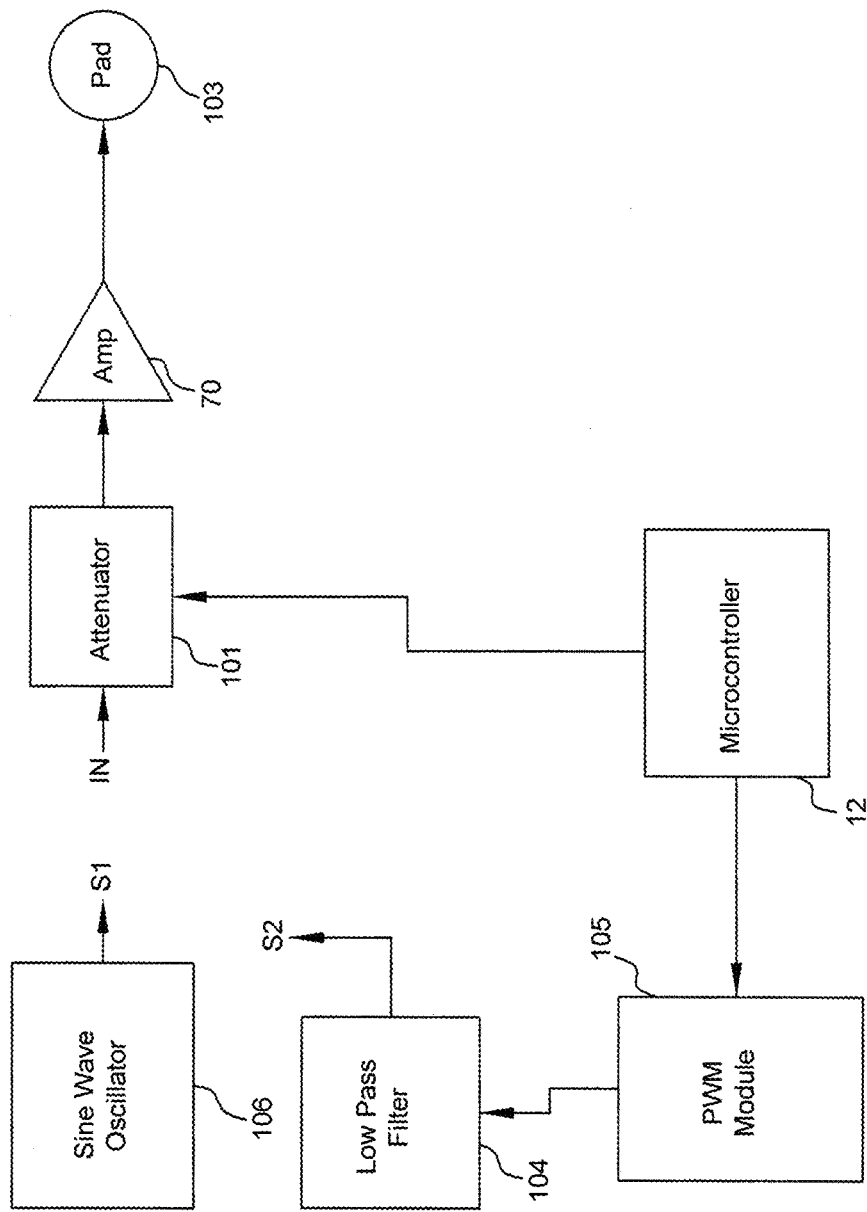
FIG. 6 illustrates the general block structure of an electrotherapeutic apparatus in accordance with some embodiments of the present disclosure.
Figure 7:
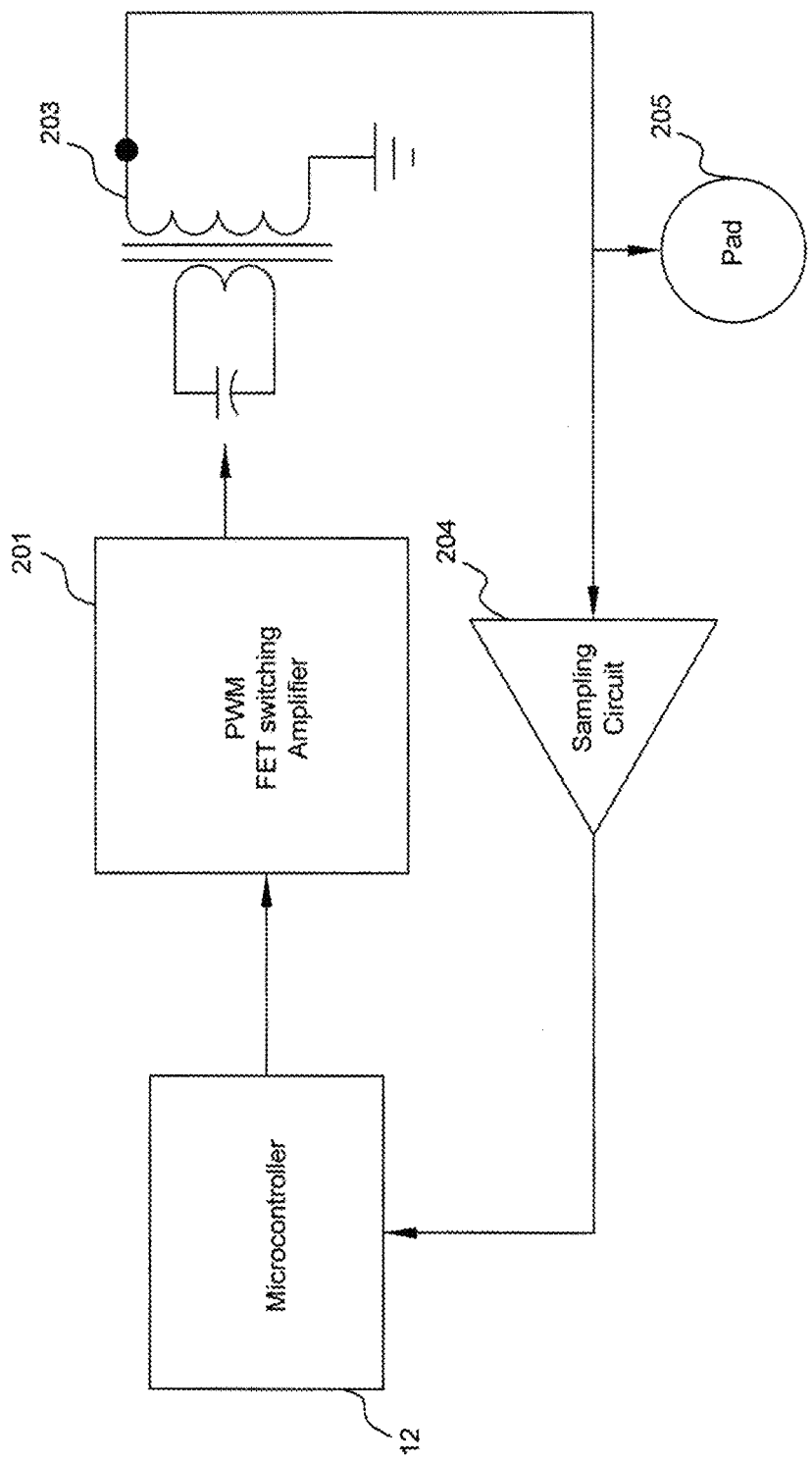
FIG. 7 illustrates the general block structure of an electrotherapeutic apparatus in accordance with some embodiments of the present disclosure.
Figure 8:
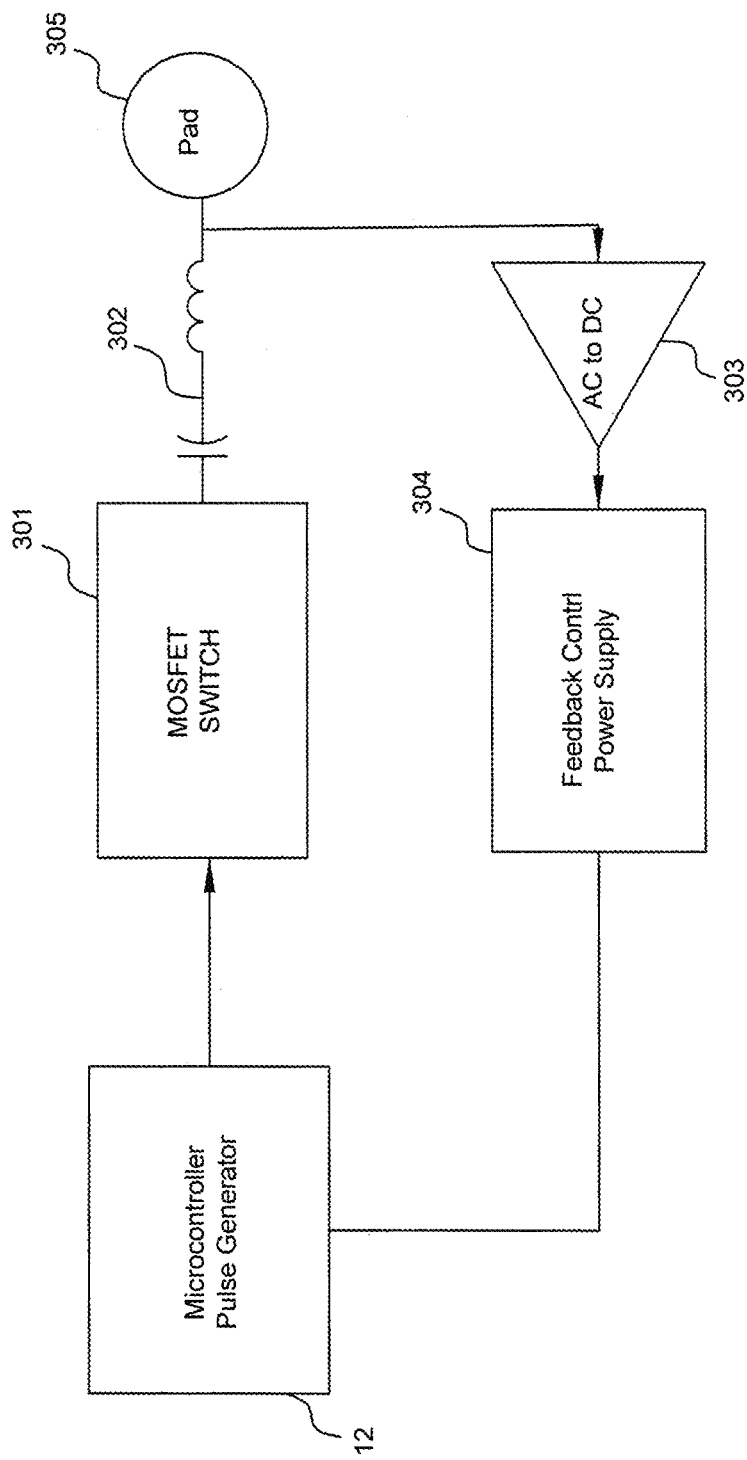
FIG. 8 illustrates the general block structure of an electrotherapeutic apparatus in accordance with some embodiments of the present disclosure.

FIGS. 6-8 illustrate the general block structures of an electrotherapeutic apparatus in accordance with some embodiments of the present disclosure. In FIG. 6, according to some embodiments, S1 represents a sine wave reference signal generated by an analog oscillator 106. S2 represents a sine wave reference signal which is derived from low-pass filtered 104 pulses generated by the pulse width modulation (PWM) 105 module within the microcontroller 12. These are two possible ways of producing the reference signals. Attenuator 101 controls the amplitude of the reference sine wave which is fed to a class AB power amplifier 70. The output of the power amplifier 70 is applied to the patient-connected electrode 103. According to some embodiments, each channel requires (either 106 or 104), 101, 70, 12 and 103.

In FIG. 7, according to various embodiments, microcontroller 12 generates a PWM signal where the relative widths of the pulses control the ultimate amplitude of the final signal. A MOSFET transistor bridge switching network 203 is driven by the PWM signal described above. The output of this bridge is a large-signal replica of the original PWM signal—Class D. This signal is passed to a low-pass filter 203 network with a cutoff frequency much lower than the pulse rate of the PWM signal. The transformer supplies voltage gain to enable the use of low voltage power supplies and low voltage monolithic or discrete device class D amplifiers. Two forms of feedback, for signal regulation, can be used: 1. A direct feedback network in the loop between the output of the switching MOSFETs to the input or 2. Using the microcontroller's 12 analog-to-digital converter to sample 204 the analog output voltage and correct this voltage by dynamically varying the PWM signal. Each channel requires 201, 203, 204 and 205.

In FIG. 8, according to various embodiments, a Class E embodiment is disclosed. Class E is a switching amplifier where 50% duty-cycle pulses drive a power switch. The pulse repetition rate is at the frequency of interest. Microcontroller 12 generates the logic-level pulses. This signal drives a MOSFET power 301 transistor whose output swings between the power supply rail and near ground. This output signal is applied to an inductor/capacitor network 302 resonant at the frequency of interest. This signal is applied to the patient-connected electrode 305. Output amplitude is entirely set by the power supply rail voltage 304. The output signal is sampled and converted to a DC correction voltage 303. This voltage is used to trim the power supply voltage thereby regulating the output signal. Each channel individually requires 301, 302, 303, 304 and 305.

Class E amplifiers are characterized by simple design, construction and relatively high efficiency (>=90%). Our therapeutic signal difference of around 122 Hz can be delivered over a band of frequencies ranging from around 1 KHz to 30 KHz. As the frequency rises the body-load impedance drops. Therefore, for a given delivered power a lower output voltage is required. Class E amplifiers require 2 amplifier channels each separately applied to one of the two electrodes. The second electrode acts as the return path for each signal. Class E amplifiers are pulse-switched tuned-output devices where the load impedance is matched to the tuned output network of the amplifier. The design of the amplifiers as disclosed according to some embodiments requires that each amplifier be tuned to some mid-band frequency (e.g.,) 10 KHz and 10.122 KHz at the average body load impedance. The operational voltage is set by the amplifier' MOSFET drain voltage. If the patient load varies it will be reflected in the measured applied voltage and current. These voltages and currents are monitored by the system microcontroller 12. The contents of look-up tables, indexed by the desired voltage and expected current, are compared to the drain voltage and the measured voltage and current. The error in expected and measured voltage and current are used by an algorithm to determine what change in operating frequencies would be required to return the output signal to its proper power density. Since, as indicated above, we have a fairly broad available frequency range it should be possible to dynamically correct for the impedance mismatch and apply the proper power to the patient load.

Transformer

For both safety and economic reasons, it is desirous to operate the device's power amplifier section at lower output voltages. In terms of safety, the use of low voltage power amplifiers guarantees that a harmless D.C. voltage level would be applied to the patient if the D.C. isolation mechanism should fail. Additionally, the use of lower supply rails lessens the complexity and cost of the power amplifier's power supplies and greatly broadens the number and types of power amplifier topologies and/or devices that can be used. This allows for more choice in determining the best power amplifier for a given price and performance. In the device transformers can supply either D.C. isolation and/or voltage gain. In one embodiment, a high coupling toroidal transformer was used to increase the device output voltage by a factor of 2.4. This kept the power supply design simple and inserted a magnetic isolation barrier between the patient and the device. In another embodiment, as discussed in more detail below, an autotransformer configuration is used to boost the output voltage from 6 V RMS to 36 V RMS. However, the inherent losses and non-linear responses found with any transformer causes its output voltage to vary as a function of the load it is connected to. This failure-to-follow or poor regulation can and does lead to patient discomfort. In order to take advantage of a transformer's voltage gain it is necessary to compensate for poor regulation.

Poor regulation can be overcome via two methods: 1. Electronically—where a sample of the output controls the gain of the output circuitry; and 2. Utilizing the microcontroller 12—where a sample of the output is converted and used by the microcontroller 12 to determine a correction to the setting of the digital intensity control.

For the configuration where the transformer has isolated primary and secondary windings, the output is sampled and returned to the amplifier section through an isolation amplifier. This is required in order to maintain the D.C. isolation barrier created by the transformer. The output of the isolation amplifier is used to either vary the bias on a transconductance amplifier or the resistance of an attenuator which controls the gain of the device's preamplifiers or power amplifier directly, in response to deviations in the output signals relative to a reference. For the autotransformer configuration, no isolation amplifier is used since this transformer-type is inherently non-isolating. In this case capacitors are used to isolate the D.C. from the output. Regulation for this transformer output is maintained by connecting the transformer primary tap or an attenuated signal developed from the high voltage tap back to the inverting input of the power amplifier. This closes the amplifier loop thereby dynamically compensating for the transformer's non-ideal behavior.

Safe Operating Limits

Paramount to any medical electrical device is the prevention or discontinuation of device's operation when it encounters an unsafe condition. For the electrotherapy device we have developed, the major unsafe condition arises when the applied current causes a rise of skin temperature above 41° C. causing a thermal burn. Another condition, which is more unpleasant than dangerous, is when the output voltage abruptly changes as a function of load change. This is perceived by the patient as a surge-like feeling. This condition is normally not associated with an increase of skin current density and as such cannot cause injury.

There are two methods which have been used to ameliorate the burn-mode of device operation. One method uses the microcontroller 12 and its software to determine if the current flow exceeds a pre-programmed limit. The output current is sampled either by a small-valued series resistor or a resistor terminated current transformer. The analog level which represents the output current is converted to a digital value and compared continuously with the preset limit. When this limit is exceeded the software turns off the power amplifier(s) or their power supplies and signals the user to the over-current condition.

The second method of safe operational control also uses a measure of the output current or a measure of the load impedance as determined from this current and applied voltage. Current monitoring is affected as with the limit control above. Voltage monitoring is performed by sampling the output voltage and converting it to a digital representation of the RMS applied voltage. Software uses these values to determine if operation is exceeding safety guidelines. For example, a drop in load impedance increases the output current. Impedance values derived from low output-level startup current and voltage values are used to determine impedance measures. An algorithm sets the allowed current limits for a given output level. If device operation falls outside of these limits, for a predetermined period, the device can shut down the device or the ability to increase signal intensity can be disabled. The use of an operational-limit algorithm and time measure is critical since there can be situations (for example, output settling or momentary electrode condition changes) where operation falls outside certain limits but are not a reflection of a device failure or other unsafe condition. Further, dynamic lowering of the device output level is used when for a given intensity the impedance changes outside of predetermined limits for a given period. This mode of operation is used to lessen or eliminate the chance of a burn when the power density rises above guideline limits. The operator can still bring down the intensity and need not stop operation as long as the maximum allowed current is never exceeded. Normal device operation is restored when the measured impedance returns to within pre-determined operational limits. If this fails to happen within a predetermined elapsed time the device is disabled, and the condition is indicated to the operator.

Timer

According to various embodiments, a timer, which can be auto-loaded with a default treatment time or have the treatment time set by the operator, is initialized and maintained by the device's system software. This timer has several uses. It shuts off the device at the end the elapsed treatment time and it acts as a reference for the safe-operation-limits software to help determine whether a time-dependent excursion outside of normal impedance boundaries is interpreted as a failure or transient event. This could include limiting the number of treatments a patient can receive within a pre-determined period. The timer can also be used to change the device output intensity as a function of a pre-loaded time-sequenced treatment protocol. The amount of aggregate treatment time accumulated by the device is updated by the timer at the end of each treatment session. This information is used to determine when battery replacement or other service procedures should be performed.

Autotransformer

It is useful if the operating voltage of the output power amplifier could remain low. This lessens losses in the switching power supply that increase as the voltages needed rise. Additionally, higher voltage amplifiers are more expensive and usually physically larger. In various embodiments, one method to achieve voltage gain is by using a transformer. Typical transformers have a primary winding and a secondary winding. They offer voltage or current gain while isolating the input circuit from the output circuit. Unfortunately, there are losses associated with the core of the transformer, the winding resistance and imprecise coupling (magnetic) between the primary and secondary winding. One way to utilize the voltage gain capabilities of a transformer is through the use of the autotransformer configuration. Here the primary and secondary share the same winding. For voltage gain assume that the input signal, in closed feedback loop with the output amplifier, is applied to N turns of wire wrapped around a ferromagnetic core (ideally a toroid) the secondary winding is just a continuation of the primary winding (electrically the same wire). To get twice the voltage from the secondary the winding is continued for another N turns on the same core. The output is taken from the end of the secondary winding. In this configuration there is tighter magnetic coupling and good output regulation (as opposed to what is found with isolated primary and secondary windings). Additionally, the autotransformer is cheaper, electrically better and smaller than a normal transformer. If desired, the output at the secondary can be attenuated and if need be phase-shifted and used to close the loop of the power amplifier. The attenuation is necessary to maintain the amplifier's differential input voltages close in value as the feedback loop requires.

Construction

Figure 9:
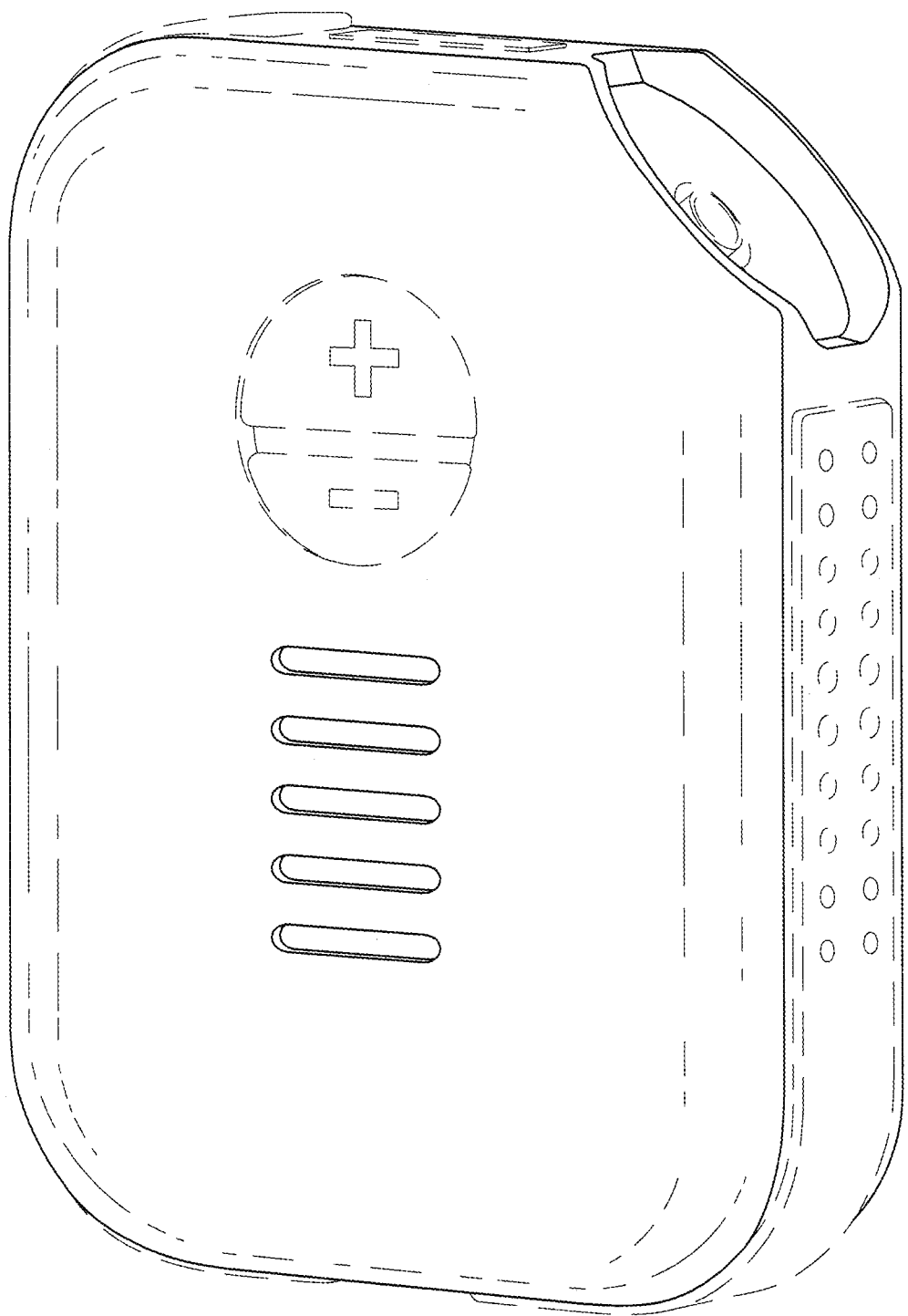
FIG. 9 is a depiction of an electrotherapeutic device in accordance with some embodiments of the present disclosure.

FIG. 9 is a depiction of an electrotherapeutic device according to some embodiments of the present disclosure. According to various embodiments, the electrotherapy device includes an option for physically manipulating the intensity of the treatment. In some embodiments, the electrotherapy device includes a communications unit for communicating with a client device to adjust the parameters remotely. For example, the electrotherapy device may be operated remotely using a client device connected via Bluetooth or WiFi communications. It should be appreciated to one of ordinary skill in the art that a client device may remotely connect to the electrotherapy device in various ways for operation. In some embodiments, the electrotherapy device may include an angled female port for connecting the electrodes. The angled port advantageously permits ease of access and wearable functionality for the electrotherapy device. In various embodiments, the angled port includes a depression for recessing the connection of the electrodes. In some embodiments, the recessed port includes a plurality of indentations configured to receive a cable attached to the male connector such that the cable is located against the side edges of the substantially rectangular device when the male connector is inserted into the female port It may be emphasized that the above-described embodiments, are merely possible examples of implementations, and merely set forth a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

Embodiments of the subject matter and the functional operations described in this specification may be implemented in electrical or electromechanical means, including the structures disclosed in this specification and their structural equivalents, or in combinations of one or more of them. Embodiments of the subject matter described in this specification may be implemented as an electrical or electromechanical unit.

Wearable System

The disclosed embodiments describe an electrotherapeutic apparatus in various configurations. Disclosed embodiments of the electrotherapeutic apparatus include features to apply a treatment to a user, including different options and controls for applying different treatments depending on particular applications. For example, disclosed embodiments may include electrotherapeutic treatment options for various users and parts of the user's body, depending on various factors. Further disclosed embodiments include wearable systems for positioning and applying the features of the disclosed electrotherapeutic devices to a user. The wearable systems may include various features for enabling an electrotherapeutic apparatus to be applied to different parts of the body, depending on a desired application.

FIG. 10A is a block diagram of an exemplary wearable system 400, according to disclosed embodiments. The wearable system 400 includes and/or is useable with an electrotherapeutic device 405. The electrotherapeutic device 405 may be a device disclosed herein, such as a device illustrated and described in relation to FIGS. 1-9. The electrotherapeutic device 405 may include electronics 407 configured to supply an electric pulse via a device connector 409. The device connector 409 may be a removable mechanical and electrical connector configured to attach to a portion of the wearable system 400. An electric pulse applied by the electrotherapeutic device 405 may be a therapeutic dose consistent with disclosed embodiments and may be particularly configured according to a target area of the user's body.

The wearable system 400 may include a garment 410. The garment 410 may be configured to be worn by a user/patient. The garment 410 may include, for example, a material body in the form of wrap-like or sleeve-like material construction configured to be worn in close contact to a targeted body part, such as a back, elbow, knee, wrist, or ankle of a user. The garment 410 may be configured to be positioned with respect to a user's body. For example, the garment 410 may be wrapped around a waist, limb, hand, foot, etc. of the user and held in place. In other embodiments, the garment 410 may be a sleeve with a built-in elastic property such that the sleeve is pulled over a part of the user's body until held in place by the elastic property at a targeted body part.

The wearable system 400 may further include one or more electrodes 420. In an exemplary embodiment, the one or more electrodes include a first electrode 420A and a second electrode 420B. Each electrode 420 may include a conductive electrode element, such as a conductive fabric electrode patch configured to apply an electrotherapeutic pulse to the wearer of the garment 410. The electrodes 420 may be integrally formed with the garment 410 in some embodiments. For example, the electrodes 420 may be a conductive fabric material making up all or a portion of the garment 410. In other embodiments, the electrodes 420 may be permanently or removably attached to the garment 410. The electrodes 420 may include a silver fabric in contact with the wearer as a conductive surface. The electrodes 420 may be strategically positioned to target a particular location on the user's body when the garment 410 is worn. In some embodiments, the electrodes 420 may be used in conjunction with a cream, gel, or other product that is applied to the skin at the targeted area to increase skin conductivity. According to disclosed embodiments, the electrode size and location for each electrode are designed to optimize delivery of high frequency signals and allow the formation inside the body of the active low frequency electrical field in the optimized desired location that would encompass and block the transmission of pain signals travelling along pain nerves.

Figure 10B:
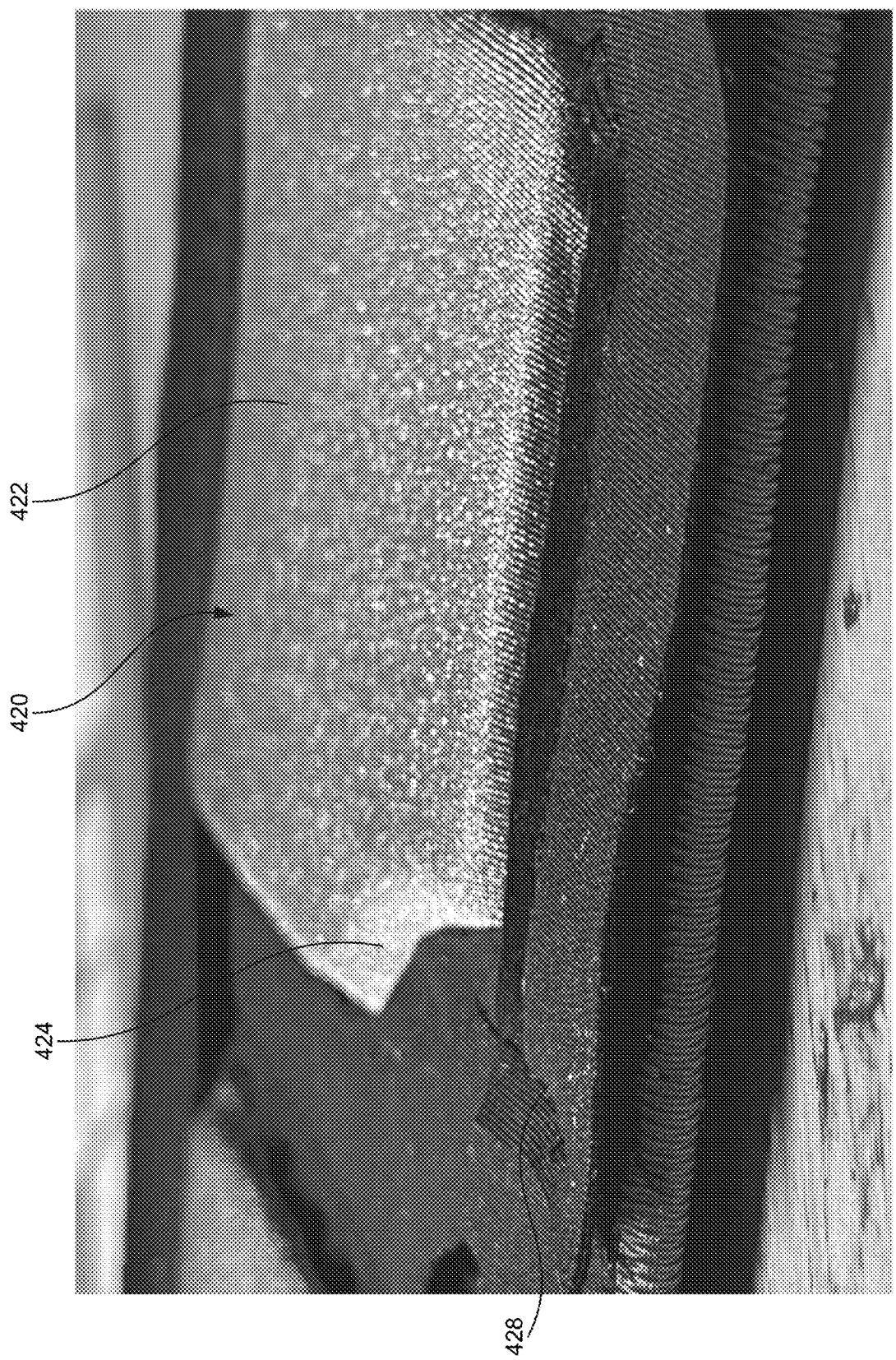
FIG. 10B is a profile view of an exemplary electrode including a raised area due to underlying memory foam material.

In at least some embodiments, the electrodes 420 are raised off the inside surface of the electrode garment by placing a compression material (e.g., memory foam) under the conductive fabric. This ensures that when the garment 410 is compressed around the area to be treated, the compression material further presses the conductive fabric against the skin to ensure a good electrical connection. FIG. 10B shows the profile of an exemplary electrode 420 from the side, illustrating the raised contact surface 422 of the conductive fabric 424 due to the thickness of the compression material (e.g., memory foam) placed underneath. This construction may be applied to any of the disclosed wearable systems and associated garments. Each disclosed garment 410 provides compression in addition to delivering pain relief into the body. Compression may act as an additional benefit to the patient, in addition to providing enhanced electrical conduction between the silver fabric and the skin.

The wearable system 400 may further include one or more electrode connectors 430. The electrode connector 430 may include a physical connector configured to connect the electrode 420 to another component, such as the electrotherapeutic device 405. The electrode connector 430 may be, for example, a metal snap connector configured as a male/female feature configured to mate with a corresponding male/female connector. The electrode connector 430 may be configured to directly or indirectly attach to the device connector 409 to complete a circuit between the electrotherapeutic device 405 and the electrode 420.

Figure 10C:
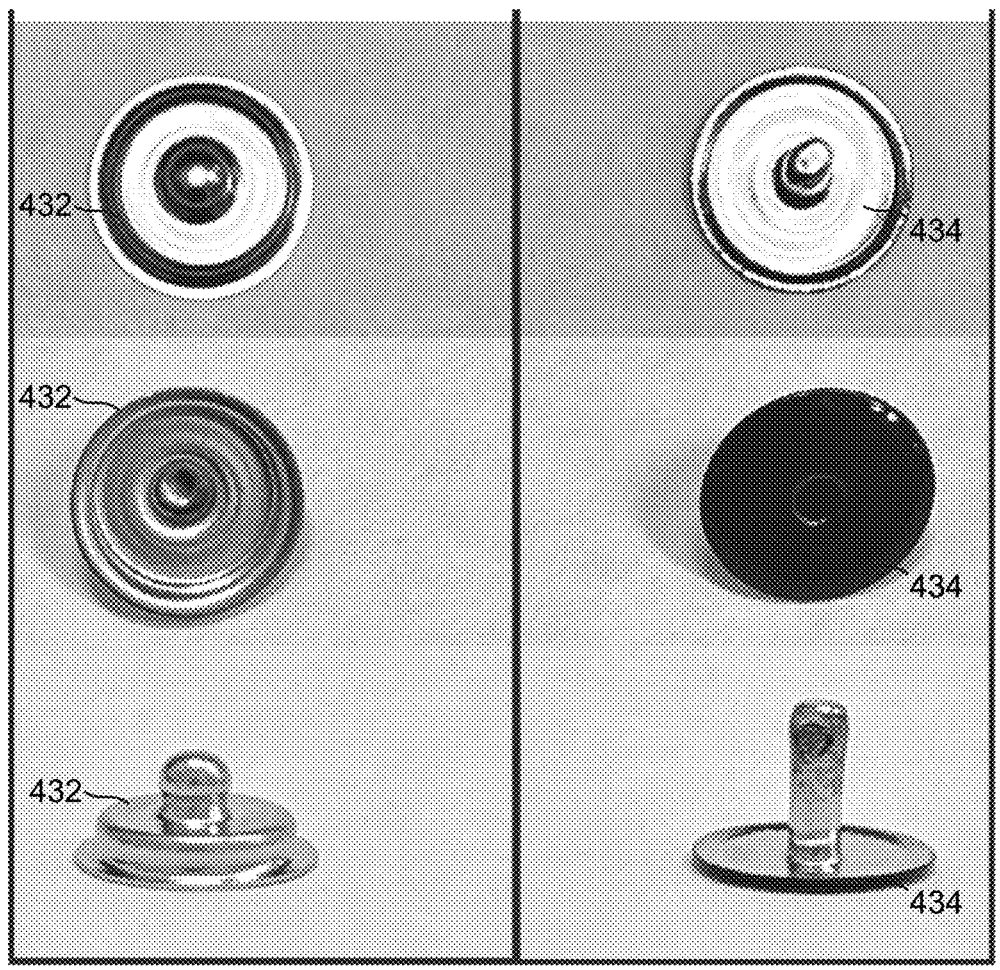
FIG. 10C is a depiction of various views of a stud and rivet that make up an exemplary electrode connector.
Figure 10D:
FIG. 10D is a depiction of the stud portion of the electrode connector on an outer surface of an exemplary garment.

FIG. 10C further illustrates an exemplary embodiment of the electrode connector 430, which may be a two-part connector including a stud 432 and a rivet 434. The stud 432 sits on the outside of the garment and the rivet 434 is inserted through the garment into the stud 432 and makes an electrical connection between the silver fabric and the stud 432. FIG. 10D illustrates the stud 432 on the exterior surface of the garment 410.

Figure 10E:
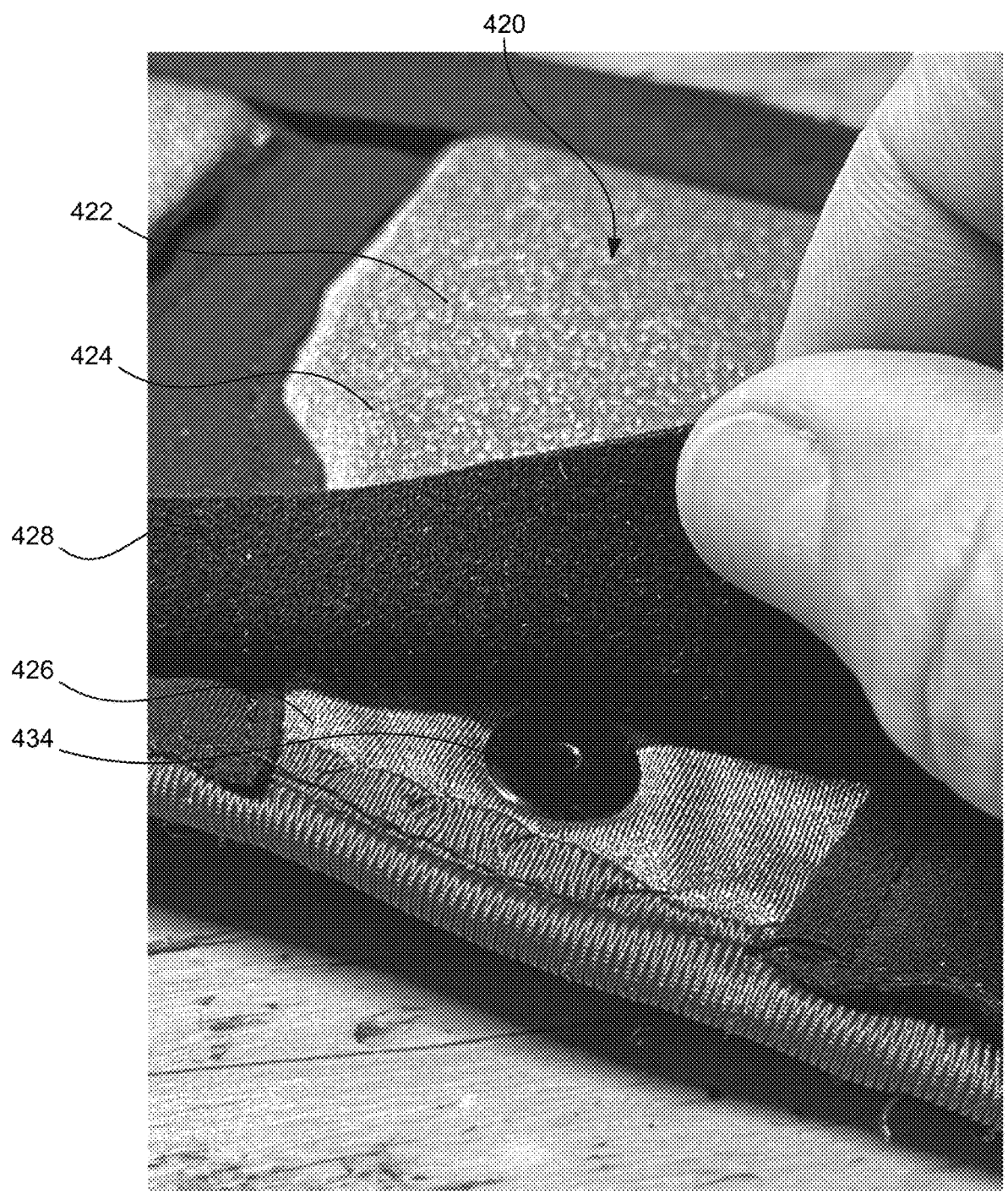
FIG. 10E is a depiction of a rivet portion of the electrode connector on an inside surface of the exemplary garment.

In an exemplary embodiment, the electrode 420 and electrode connector 430 may be configured to prevent the connector from being in a contact surface area of the electrode 420. If the electrode connector 430 were to contact the wearer, a hot spot or stinging sensation may be experienced by the wearer. The garment 410 may be configured to help prevent this occurrence. In one example, the bottom side of the rivet 434 which is exposed on the conductive fabric 424 may be coated with a nonconductive coating to prevent stinging. In another embodiment, the contact surface 422 of the electrode 420 (e.g., silver fabric) is extended off of the raised compression material and the electrode connector 430 (e.g., the rivet 434) is located at this recessed level 426 on the conductive fabric 424 below the raised contact surface 422 portion of the conductive fabric 424 that touches the skin. FIGS. 10B and 10E further illustrates this feature. A cover material 428 may be non-conductive and configured to cover the recessed level 426 of the conductive fabric 424 of the electrode 420.

The wearable system 400 may also include an intermediate wire 440 configured to connect the electrode connector 430 to the device connector 409 of the therapeutic device 405. FIG. 11 is an embodiment of an exemplary intermediate wire 440. The intermediate wire 440 may include a first wire connector 442 configured to operably attach to the electrode connector 430 and a second wire connector 444 configured to operably attach to the device connector 409. For example, the first wire connector 442 may be a connector configured to removably "snap" to the electrode connector 430. The second wire connector 444 may be a buckle-type connector in some embodiments configured to attach to mating device connector 409 (e.g., in the form of a similar buckle-type connector).

In some embodiments, the wearable system 400 may further include a wire management feature 450. The wire management feature may include a built-in feature of the garment 410 configured to receive and/or manage at least a portion of a connection between the electrode 420 and the electrotherapeutic device 405. For example, the wire management feature 450 may include a channel configured to receive and route the intermediate wire 440 from the electrode connector 430 to the electrotherapeutic device 405.

In some embodiments, the wearable system 400 may further include a carrier 460 for the electrotherapeutic device 405. For example, the garment 410 may include a pocket, pouch, or other storage and/or attachment feature configured to hold and/or store the electrotherapeutic device of FIG. 9. In this way, the electrotherapeutic device 405 may be readily accessible and carried by the garment 410. In some embodiments, the electrotherapeutic device 405 may be built-in and/or integrally formed with the garment 410. For example, the garment 410 may include built-in circuitry and/or processing components for routing electrical pulses to the electrode 420.

In some embodiments, the wearable system 400 may also include an attachment mechanism 470. The attachment mechanism 470 may include, for example, an elastic strap, mechanical connector, loop, hook and loop fastener, etc. that holds the garment 405 in place on the user's body. The attachment mechanism 470 may be particularly configured depending on the targeted part of the body. The attachment mechanism 470, in at least some embodiments, provides compression directly over the application area (e.g., the area corresponding location of the one or more electrodes 420) to maintain electrical contact with targeted part of the user's body.

The wearable system 400 encompasses multiple embodiments that may include configurations that are tailored to certain parts of the body. For example, embodiments, may include a lower back wearable system 500, knee wearable system 600, ankle/foot wearable system 700, elbow wearable system 800, wrist/hand wearable system 900, shoulder wearable system 1000, and head/neck wearable system 1100. However, it should be understood that other embodiments may be formed to target other parts of the body.

The wearable system 400 is configured to provide a therapeutic signal to the targeted area of the user through the first and second electrodes 420A, 420B. The therapeutic signal may be as described herein with respect to FIGS. 1-9. For example, the therapeutic signal may be a combination of a first and second signal that is delivered through the electrode 420. The therapeutic signal may include a voltage level. In some embodiments, the user increases the voltage to tolerance at whatever location is being treated. As the body adapts to the electrical field, the sensation felt by the patient diminishes and the user needs to increase the voltage to maintain a strong steady state sensation from the electrical field. The rate of increase in voltage may be greater in the first 5 minutes of treatment; then the rate of increase in voltage may decrease over the remainder of a 30-minute treatment, for example. The voltage may also be selected based on the target area. For example, some patients can tolerate a higher voltage (high level of stimulation) in the foot-ankle and knee areas; a medium voltage level (medium level of stimulation) in the low back and shoulder areas; and a lower voltage level (lower level of stimulation) in the hand-wrist, elbow and neck areas.

FIGS. 12A and 12B are front and back views of a first exemplary embodiment of the lower back wearable system 500. The lower back wearable system 500 may include a garment 510. The garment 510 may be constructed as a belt configured to be worn around a waist of a user. The garment 510 may include a fabric material and include a tapered design to include a larger surface area at an application area 512 configured to be positioned adjacent to the lower back of a user. The garment 510 may include attachment mechanism 514 in the form of mating hook and loop fasteners 516 and/or optional tightening straps 518. It is also contemplated that garment 510 may be constructed as a sleeve, and made of stretch material, such that garment 510 can be pulled onto the waist of a user, without the need to wrap garment 510, where the stretch material secures garment 510 into place. For example, in some embodiments, the attachment mechanism 514 may be a built-in elastic property, such as may be present in a sleeve embodiment, and not necessarily an additional feature such as fasteners 516 and/or straps 518.

The garment 510 may include an interior surface 520 configured to contact the user and an opposite exterior surface 522. The lower back wearable system 500 may further comprise one or more electrodes 524 on the interior surface 520 and configured to contact the user. The electrodes 524 may be built-in conductive fabric electrodes, for example. The one or more electrodes 524 may include two electrode pads positioned in the application area 512 and configured to contact a lower back area of a user. In an exemplary embodiment, the one or more electrodes 524 are positioned on opposing sides of a center line 526 of the garment 510 to provide two spaced-apart electrotherapeutic locations for the lower back wearable system 500. While two electrodes 524 are shown, it should be understood that disclosed embodiments are not limited to any particular number of electrodes.

The garment 510 may further include at least one electrode connector 528. The garment 510 may include an electrode connector 528 for each electrode 524. The electrode connector 528 may include a mechanical and electrical connection point for the respective electrode 524. In an exemplary embodiment, the electrode connector 528 is a snap connector, such as a male snap element configured to mate with a female snap element. The electrode connector 528 may include a conductive material (e.g., metal) such that a functional electrical connection may be established with the electrode 524 via the electrode connector 528. In an exemplary embodiment, the electrode connector 528 may have a non-conductive coating on the bottom side of the snap connector (e.g., the rivet) that is exposed on the face of the electrode 524. This non-conductive coating helps to prevent the patient from feeling a hot spot or stinging sensation at the location of the electrode connector 528. In an exemplary embodiment, the electrode connectors 528 are exposed on the exterior surface 522 to facilitate connection to an intermediate wire 440.

In an exemplary embodiment, the electrode connectors 528 are positioned on the exterior surface 522 above or below the location of the compression material (e.g., memory foam) which sits beneath and raises the electrode surface above the interior surface 520. The conductive surface of the electrode 524 continues above or below the compression material directly onto the interior surface 520. The electrode connector 528 may be placed at this location through the electrode surface but off of and away from the compression material. A nonconductive material may be applied to cover up the portion of the conductive fabric and the electrode connector 528 that sits recessed below the compression material. This type of construction helps to eliminate stinging and leave a smooth raised surface for the conductive electrode 524.

The garment 510 may further include channels 530. The channels 530 may be wire management features configured to receive and route a wire connector between the electrode connectors 528 and an electrotherapeutic device. For example, each channel 530 may be positioned adjacent to a respective electrode connector 528 and configured to route intermediate wire 440 from the electrode connector 528 to another position (e.g., beneath or above the garment 510).

The first wire connector 442 of each intermediate wire 440 may be configured to attach to a respective electrode connector 528.

FIGS. 13A and 13B include another exemplary embodiment of a lower back wearable system 500A, including another design with similar features. For examples, the lower back wearable system 500A may include a different design for tightening straps 518A and a centered location for a connection to the intermediate wires 440.

Figure 14A:
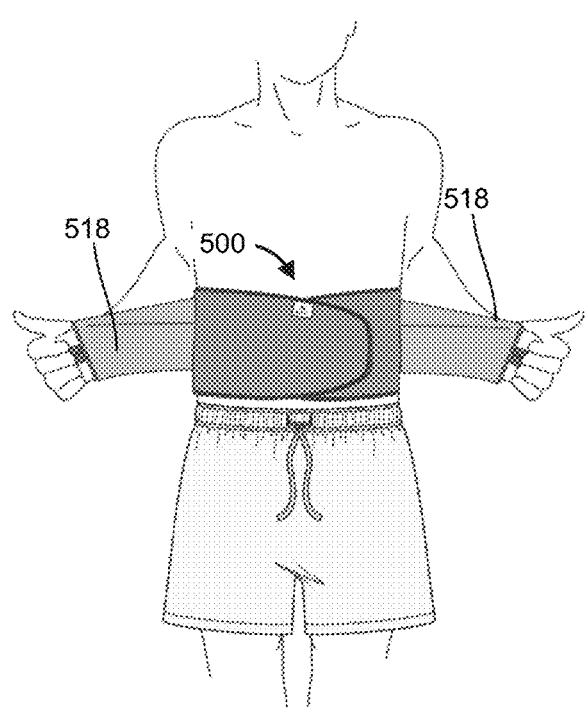
FIG. 14A is a front view of the lower back wearable system on a user prior to tightening secondary straps in accordance with some embodiments of the present disclosure.
Figure 14B:
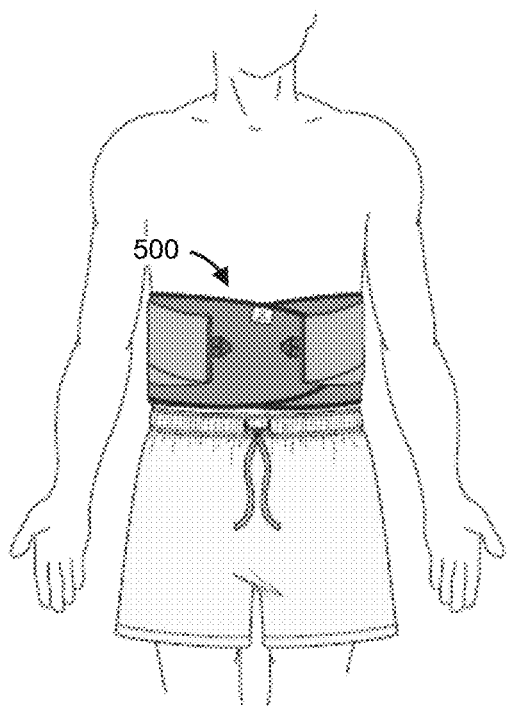
FIG. 14B is a front view of the lower back wearable system on a user after tightening secondary straps in accordance with some embodiments of the present disclosure.
Figure 15:
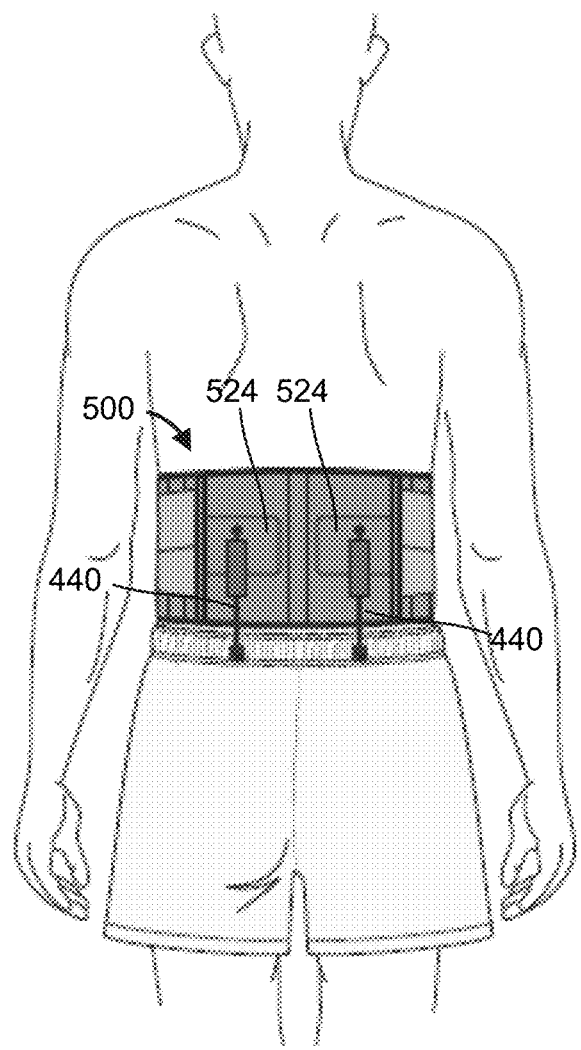
FIG. 15 is a rear view of the lower back wearable system on a user in accordance with some embodiments of the present disclosure.

FIGS. 14A, 14B, and 15 further illustrate the lower back wearable system 500 being worn by a user. The garment 510 is held in place by the attachment mechanism 514 such that the electrodes 524 are positioned at a target area—the lower back of the user. A shown in FIG. 14A, the user can pull the tightening straps 518 toward the front of the user and re-attach them to the exterior surface 522, as shown in FIG. 14B. Tightening straps 518 start at the centerline of the back of the device over the user's spine and provide compression directly over the back side of both electrodes 524, as well as cover over the intermediate wires 440, electrode connectors 528 and channels 530.

Intermediate wires 440 are connected to the electrode connectors 528 and routed through the channels 530. The second wire connectors 444 are easily accessible for functional connection to an electrotherapeutic device according to disclosed embodiments.

FIGS. 16A and 16B are front and back views of a first embodiment of the knee wearable system 600. The knee wearable system 600 may include a garment 610. The garment 610 may be constructed as a flexible wrap configured to be worn around a knee area of a user. The garment 610 may include a fabric material and include an application area 612 configured to be positioned adjacent to a knee area of a user. The garment 610 may further include attachment mechanism 614 in the form of an elastic strap 616 attached to the application area 612 for securing the garment 610 in place. The elastic strap 616 also provides compression directly over the electrodes 624 and as a result it provides better electrical conduction through the skin. The garment 610 may also include one or more loops 618 for routing the elastic strap 616 and a fastener 619 (e.g., hook and loop fastener) for securing the elastic strap 616 to the application area 612. It is also contemplated that garment 610 may be constructed as a sleeve, and made of stretch material, such that garment 610 can be pulled onto the knee of a user, without the need to wrap garment 610, where the stretch material secures garment 610 into place. For example, in some embodiments, the attachment mechanism 614 may be a built-in elastic property, such as may be present in a sleeve embodiment, and not necessarily an additional feature such as strap 616, loops 618 and/or fastener 619.

The garment 610 may include an interior surface 620 configured to contact the user and an opposite exterior surface 622. The knee wearable system 600 may further comprise one or more electrodes 624 on the interior surface 620 and be configured to contact the user. The electrodes 624 may be built-in conductive fabric electrodes, for example. The one or more electrodes 624 may include two electrode pads positioned in the application area 612 and configured to contact a knee area of a user. In an exemplary embodiment, the one or more electrodes 624 are positioned on opposing sides of a knee cap hole 626 built-in to the garment 610 to provide two spaced-apart electrotherapeutic locations for the knee wearable system 600. The electrodes 624 may be rectangular-shaped with cutout-portions 627 configured to follow an outline of the knee cap hole 626. In this way, the electrodes 624 may be positioned such that treatment is not applied directly to the user's knee cap. While two electrodes 624 are shown, it should be understood that disclosed embodiments are not limited to any particular number of electrodes.

The garment 610 may further include at least one electrode connector 628. The garment 610 may include an electrode connector 628 for each electrode 624. The electrode connector 628 may include a mechanical and electrical connection point for the respective electrode 624. In an exemplary embodiment, the electrode connector 628 is a snap connector, such as a male snap element configured to mate with a female snap element. The electrode connector 628 may include a conductive material (e.g., metal) such that a functional electrical connection may be established with the electrode 624 via the electrode connector 628. In an exemplary embodiment, the electrode connector 628 may have a non-conductive coating on the bottom side of the snap connector (e.g., rivet) that is exposed on the face of the electrode 624. This non-conductive coating helps to prevent the patient from feeling a hot spot or stinging sensation at the location of the snap connector. In an exemplary embodiment, the electrode connectors 628 are positioned on the exterior surface 622.

In an exemplary embodiment, the electrode connectors 628 are positioned on the exterior surface 622 above or below the location of the compression material (e.g., memory foam) which sits beneath and raises the electrode surface above the interior surface 620. The conductive surface of each electrode 624 may continue above or below the memory foam directly onto the interior surface 620. The electrode connector 628 may be placed at this location through the electrode surface, spaced from the compression material. A nonconductive material may be applied to cover up the portion of the conductive fabric and the electrode connector 628 that sits recessed below the compression material. This type of construction eliminates stinging and leaves a smooth raised surface for the conductive electrode 624.

The garment 610 may further include channels 630. The channels 630 may be wire management features configured to receive and route a wire connector between the electrode connectors 628 and an electrotherapeutic device. For example, each channel 630 may be positioned adjacent to a respective electrode connector 628 and configured to route intermediate wire 440 from the electrode connector 628 to another position (e.g., beneath or above the garment 610). The first wire connector 442 of each intermediate wire 440 may be configured to attach to a respective electrode connector 628.

FIGS. 16C and 16D further illustrate the knee wearable system 600 being worn by a user. The garment 610 is held in place by the elastic strap 616 such that the electrodes 624 are positioned at a target area—the front leg around the area of the knee of the user. The user's knee cap is positioned in the knee cap hole 626. Intermediate wires 440 are connected to the electrode connectors 628 and routed through the channels 630. The second wire connectors 444 are easily accessible for functional connection to an electrotherapeutic device according to disclosed embodiments. FIG. 16C is an illustration of a right leg of a user and FIG. 16D is an illustration of a left leg of a user. The application area 612 may be generally symmetrical across a vertical center line through the knee cap hole 626 such that the knee wearable system 600 is configured to be worn on either the right or left leg as shown.

Figure 17A:
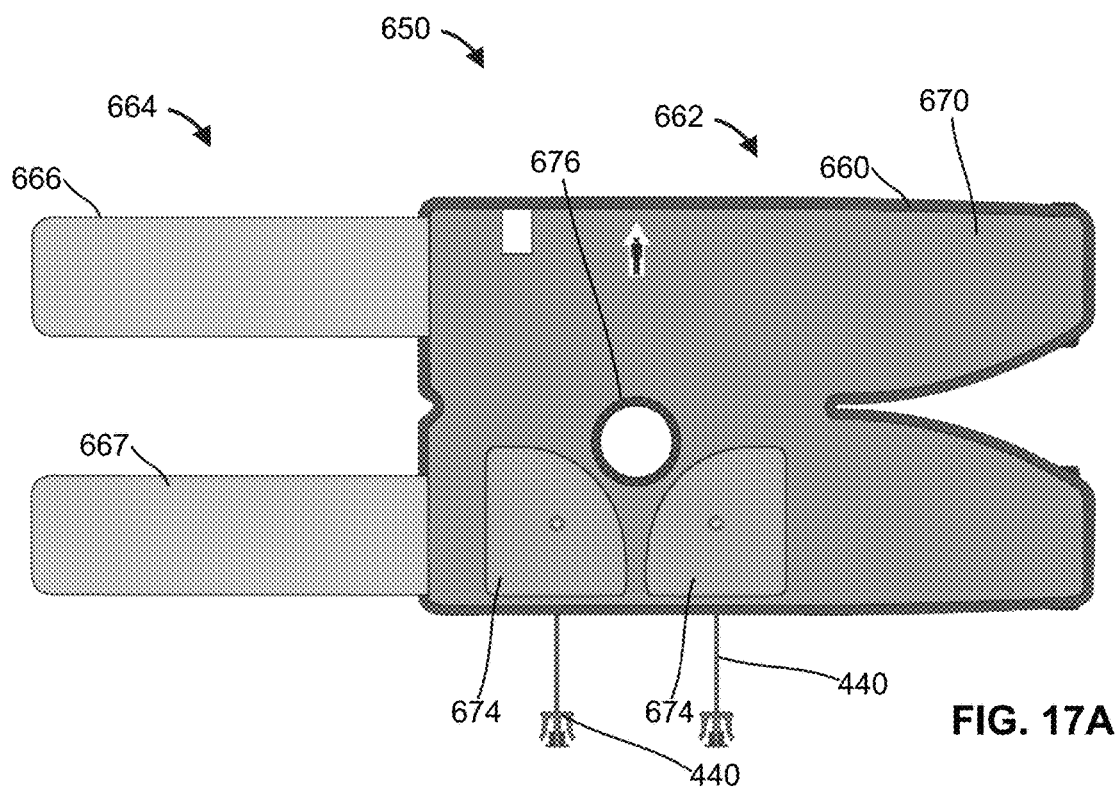
FIG. 17A is an inside view of a knee wearable system in accordance with some embodiments of the present disclosure.
Figure 17B:
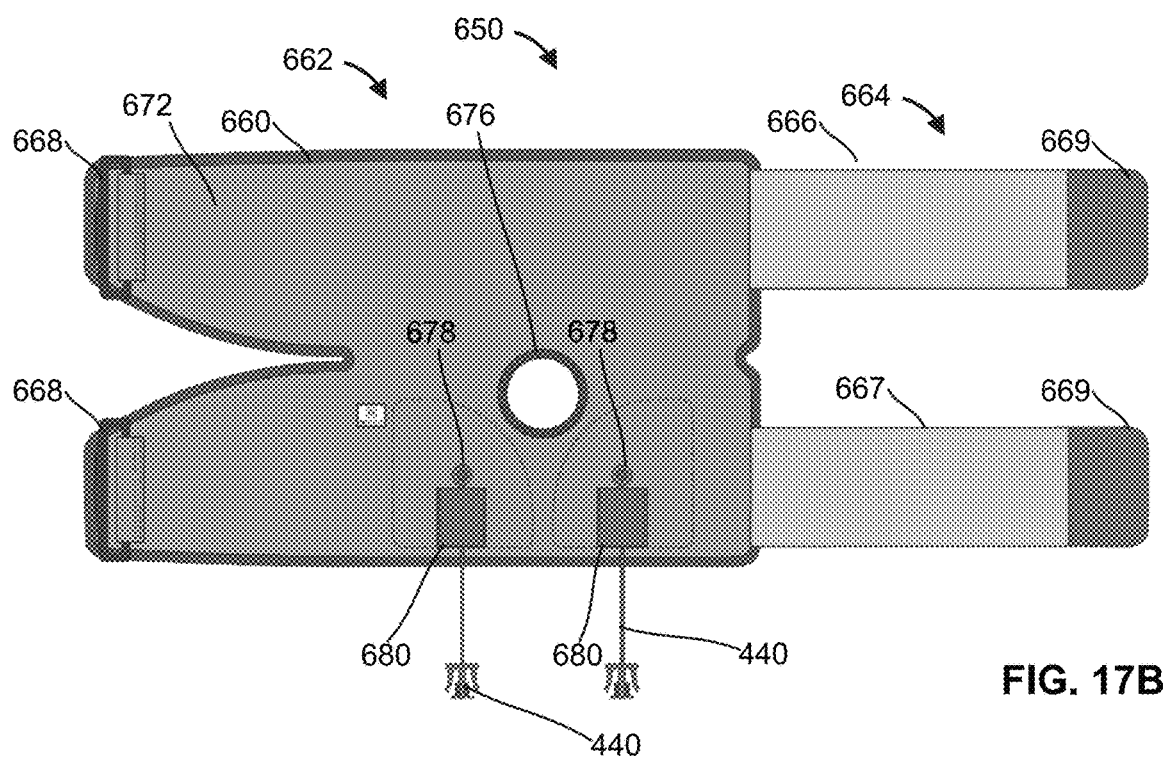
FIG. 17B is an outside view of the knee wearable system in accordance with some embodiments of the present disclosure.
Figure 18C:
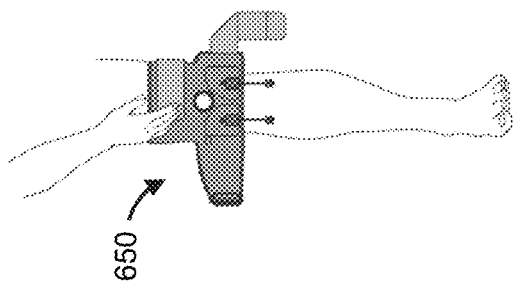
FIGS. 18A-18E are a depiction of the knee wearable system on a right leg of a user in accordance with some embodiments of the present disclosure.
Figure 18E:
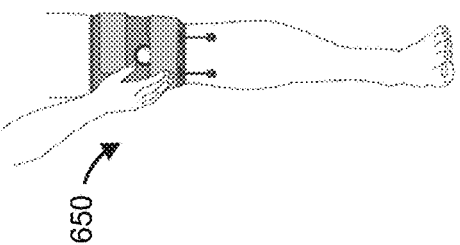
Figure 18B:
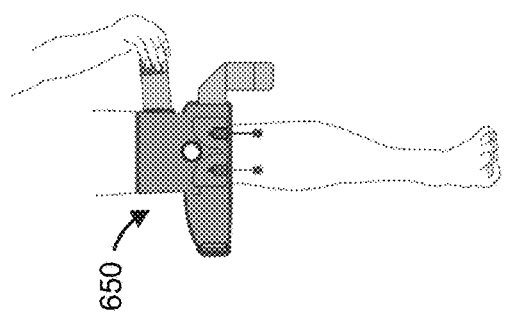
Figure 18D:
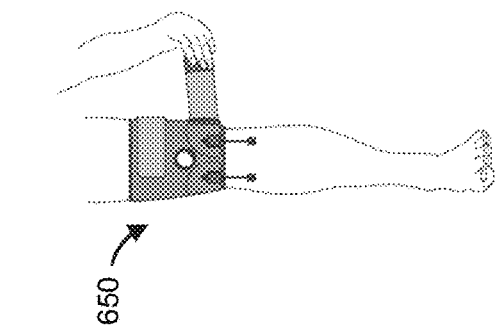
Figure 18A:
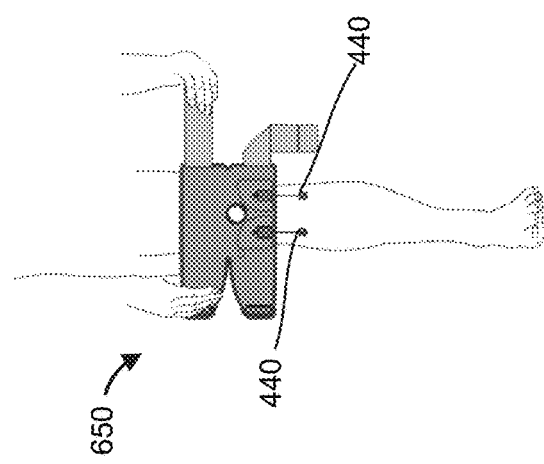

FIGS. 17A and 17B are front and back views of a second embodiment of the knee wearable system 650. The knee wearable system 650 may include a garment 660. The garment 660 may be constructed as a flexible wrap configured to be worn around a knee area of a user. The garment 660 may include a fabric material and include an application area 662 configured to be positioned adjacent to a knee area of a user. The garment 660 may further include attachment mechanism 664 in the form of a first elastic strap 666 attached to the application area 662 and a second elastic strap 667 attached to the application area 662 for securing the garment 660 in place. The elastic straps 666 and 667 also provide compression. The elastic strap 667 provides compression directly over the electrodes 674 to provide better electrical conduction through the skin. The garment 660 may also include one or more loops 668 for routing the elastic straps 666, 668 and a fastener 669 (e.g., hook and loop fastener) for securing the elastic straps 666, 667 to the application area 662. It is also contemplated that garment 660 may be constructed as a sleeve, and made of stretch material, such that garment 660 can be pulled onto the knee of a user, without the need to wrap garment 660, where the stretch material secures garment 660 into place. For example, in some embodiments, the attachment mechanism 664 may be a built-in elastic property, such as may be present in a sleeve embodiment, and not necessarily an additional feature such as straps 666, 667, loops 668 and/or fastener 669.

The garment 660 may include an interior surface 670 configured to contact the user and an opposite exterior surface 672. The knee wearable system 650 may further comprise one or more electrodes 674 on the interior surface 670 and be configured to contact the user. The electrodes 674 may be built-in conductive fabric electrodes, for example. The one or more electrodes 674 may include two electrode pads positioned in the application area 662 and configured to contact a knee area of a user. In an exemplary embodiment, the one or more electrodes 674 are positioned on opposing sides of a knee cap hole 676 built-in to the garment 660 to provide two spaced-apart electrotherapeutic locations for the knee wearable system 650. The electrodes 674 may be generally shaped similar to a quarter-circle, with two straight edges connected by a curved edge. It should be understood, however, that the electrodes 674 can take other shapes depending on the application and/or size of the area to be contacted. While two electrodes 674 are shown, it should be understood that disclosed embodiments are not limited to any particular number of electrodes.

The garment 660 may further include at least one electrode connector 678. The garment 660 may include an electrode connector 678 for each electrode 674. The electrode connector 678 may include a mechanical and electrical connection point for the respective electrode 674. In an exemplary embodiment, the electrode connector 678 is a snap connector, such as a male snap element configured to mate with a female snap element. The electrode connector 678 may include a conductive material (e.g., metal) such that a functional electrical connection may be established with the electrode 674 via the electrode connector 678. In an exemplary embodiment, the electrode connector 678 may have a non-conductive coating on the bottom side of the snap connector (e.g., rivet) that is exposed on the face of the electrode 674. This non-conductive coating helps to prevent the patient from feeling a hot spot or stinging sensation at the location of the snap connector. In an exemplary embodiment, the electrode connectors 628 are positioned on the exterior surface 672.

In an exemplary embodiment, the electrode connectors 678 are positioned on the exterior surface 672 above or below the location of the compression material (e.g., memory foam) which sits beneath and raises the electrode surface above the interior surface 670. The conductive surface of each electrode 674 may continue above or below the memory foam directly onto the interior surface 670. The electrode connector 678 may be placed at this location through the electrode surface, spaced from the compression material. A nonconductive material may be applied to cover up the portion of the conductive fabric and the electrode connector 678 that sits recessed below the compression material. This type of construction eliminates stinging and leaves a smooth raised surface for the conductive electrode 674.

The garment 660 may further include channels 680. The channels 680 may be wire management features configured to receive and route a wire connector between the electrode connectors 678 and an electrotherapeutic device. For example, each channel 680 may be positioned adjacent to a respective electrode connector 678 and configured to route intermediate wire 440 from the electrode connector 678 to another position (e.g., beneath or above the garment 660). The first wire connector 442 of each intermediate wire 440 may be configured to attach to a respective electrode connector 678.

FIGS. 18A-E and 19A-E further illustrate the knee wearable system 650 being attached and worn by a user. The garment 650 is held in place by the elastic straps 666, 667 such that the electrodes 674 are positioned at a target area—the front leg around the area of the knee of the user. The user's knee cap is positioned in the knee cap hole 676. Intermediate wires 440 are connected to the electrode connectors 678 and routed through the channels 680. The second wire connectors 444 are easily accessible for functional connection to an electrotherapeutic device according to disclosed embodiments. FIGS. 18A-E are illustrations of attachment of the garment 650 to the right leg of a user and FIGS. 19A-E are illustrations of attachment of the garment 650 to a left leg of a user.

Figure 20A:
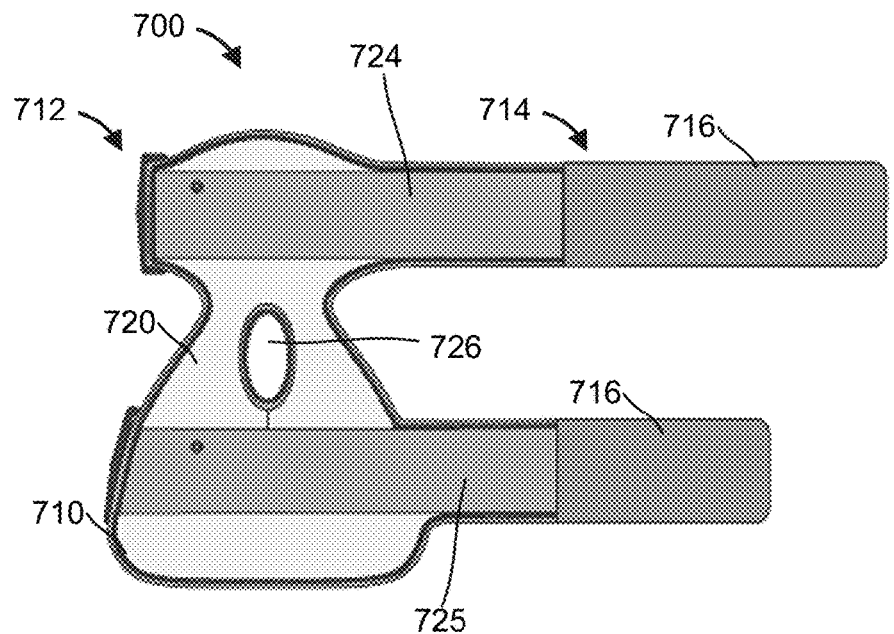
FIG. 20A is an inside view of an ankle/foot wearable system in accordance with some embodiments of the present disclosure.
Figure 20B:
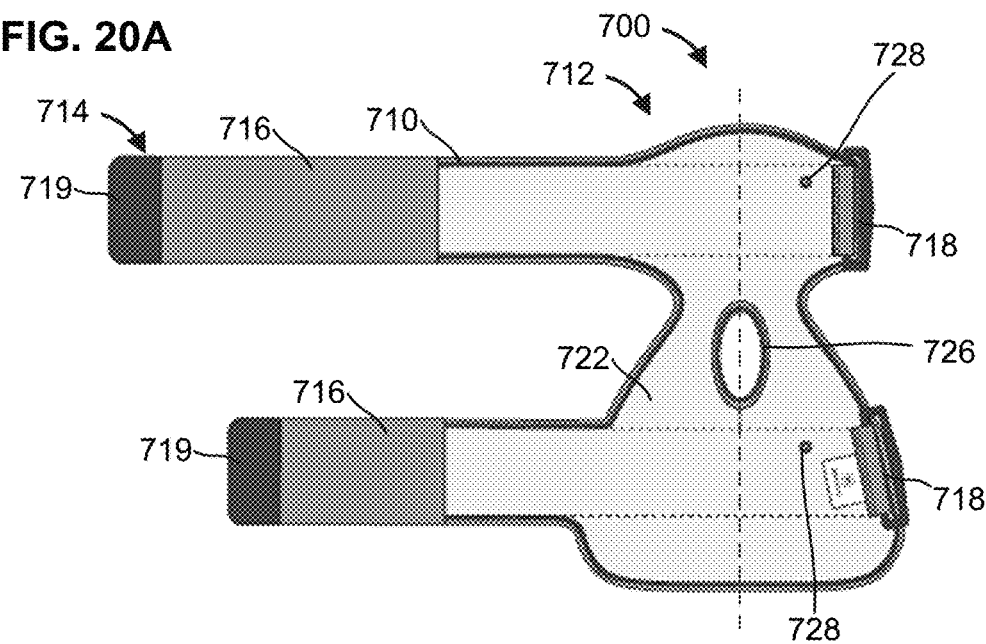
FIG. 20B is an outside view of the ankle/foot wearable system in accordance with some embodiments of the present disclosure.

FIGS. 20A and 20B are front and back views of a first exemplary embodiment of the ankle/foot wearable system 700. The ankle/foot wearable system 700 may include a garment 710. The garment 710 may be constructed as a flexible wrap configured to be worn around at least a portion of the ankle and/or foot of a user. The garment 710 may include a fabric material and include an application area 712 configured to be positioned adjacent to an ankle and foot area of a user. The garment 710 may further include attachment mechanism 714 in the form of one or more elastic straps 716 attached to the application area 712 for securing the garment 710 in place. The garment 710 may also include one or more loops or rings 718 for routing a respective elastic strap 716 and a fastener 719 (e.g., hook and loop fastener) for securing each elastic strap 716 to the application area 712. It is also contemplated that garment 710 may be constructed as a sleeve, and made of stretch material, such that garment 710 can be pulled onto the foot and ankle of a user, without the need to wrap garment 710, where the stretch material secures garment 710 into place. For example, in some embodiments, the attachment mechanism 714 may be a built-in elastic property, such as may be present in a sleeve embodiment, and not necessarily an additional feature such as strap 716, loops 718, and/or fastener 719.

The garment 710 may include an interior surface 720 configured to contact the user and an opposite exterior surface 722. The ankle/foot wearable system 700 may further comprise one or more electrodes 724, 725 on the interior surface 720 and configured to contact the user. The electrodes 724, 725 may be built-in conductive fabric electrodes, for example. The one or more electrodes 724, 725 may include two electrode pads positioned in the application area 712 and configured to contact a foot and/or ankle area of user. While two electrodes 724, 725 are shown, it should be understood that disclosed embodiments are not limited to any particular number of electrodes.

In an exemplary embodiment, each electrode 724, 725 is configured as a rectangular strip configured to wrap around a portion of the user to provide a wide contact area. For example, the electrode 724 may be configured to wrap just at or above an ankle of a user and the electrode 725 may be configured to wrap around a portion of the foot of the user.

The garment 710 may further include a heel hole 726 to receive and accommodating a heel of the user. The heel hole 726 may be positioned between the electrodes 724, 725. The application area 712 may be generally symmetrical about a vertical axis passing through the heel hole 726. In this way, the garment 710 may be worn on either the left or right foot of a user. The garment 710 may include an hourglass shape with a larger bottom portion for wrapping around the foot of wearer and a relatively smaller top portion for wrapping around an ankle/lower leg of the user.

The garment 710 may further include at least one electrode connector 728. The garment 710 may include an electrode connector 728 for each electrode 724 and 725. The electrode connector 728 may include a mechanical and electrical connection point for the respective electrode 724 and 725. In an exemplary embodiment, the electrode connector 728 is a snap connector, such as a male snap element configured to mate with a female snap element. The electrode connector 728 may include a conductive material (e.g., metal) such that a functional electrical connection may be established with the electrode 724 and 725 via the electrode connector 728. In an exemplary embodiment, the electrode connector 728 may have a non-conductive coating on the bottom side of the snap connector (e.g., rivet) that is exposed on the face of each electrode 724, 725. This non-conductive coating helps to prevent the patient from feeling a hot spot or stinging sensation at the location of the snap connector. In an exemplary embodiment, the electrode connectors 728 are positioned on the exterior surface 722.

In an exemplary embodiment, the electrode connectors 728 are positioned on the exterior surface 722 above or below the location of the compression material (e.g., memory foam) which sits beneath and raises the electrode surface above the interior surface 720. The conductive surface of each electrode 724, 725 may continue above or below the memory foam directly onto the interior surface 720. The electrode connector 728 may be placed at this location through the electrode surface, spaced from the compression material. A nonconductive material may be applied to cover up the portion of the conductive fabric and the electrode connector 728 that sits recessed below the compression material. This type of construction eliminates stinging and leaves a smooth raised surface for the conductive electrodes 724, 725.

The garment 710 may be configured to operate in conjunction with one or more of the intermediate wires 440. The intermediate wires 440 may be positioned to extend from each electrode connector 728 to another position (e.g., beneath or above the garment 710). The first wire connector 442 of each intermediate wire 440 may be configured to attach to a respective electrode connector 728. The electrode connectors 728 may be positioned to be covered by the elastic straps 716 such the elastic straps may act as a hold-down for at least a portion of the intermediate wires 440.

Figure 21A:
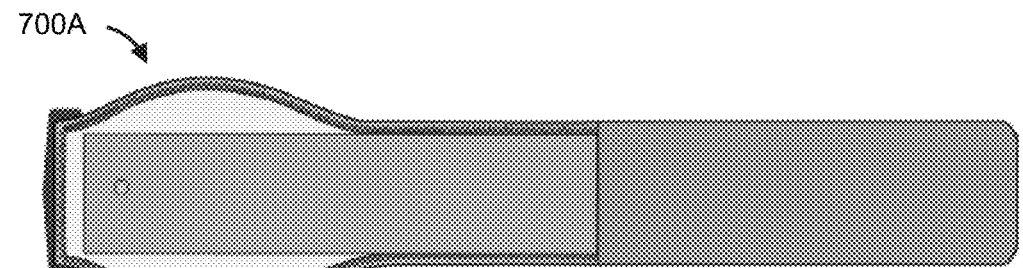
FIG. 21A is an inside view of an ankle/foot wearable system in accordance with some embodiments of the present disclosure.
Figure 21B:
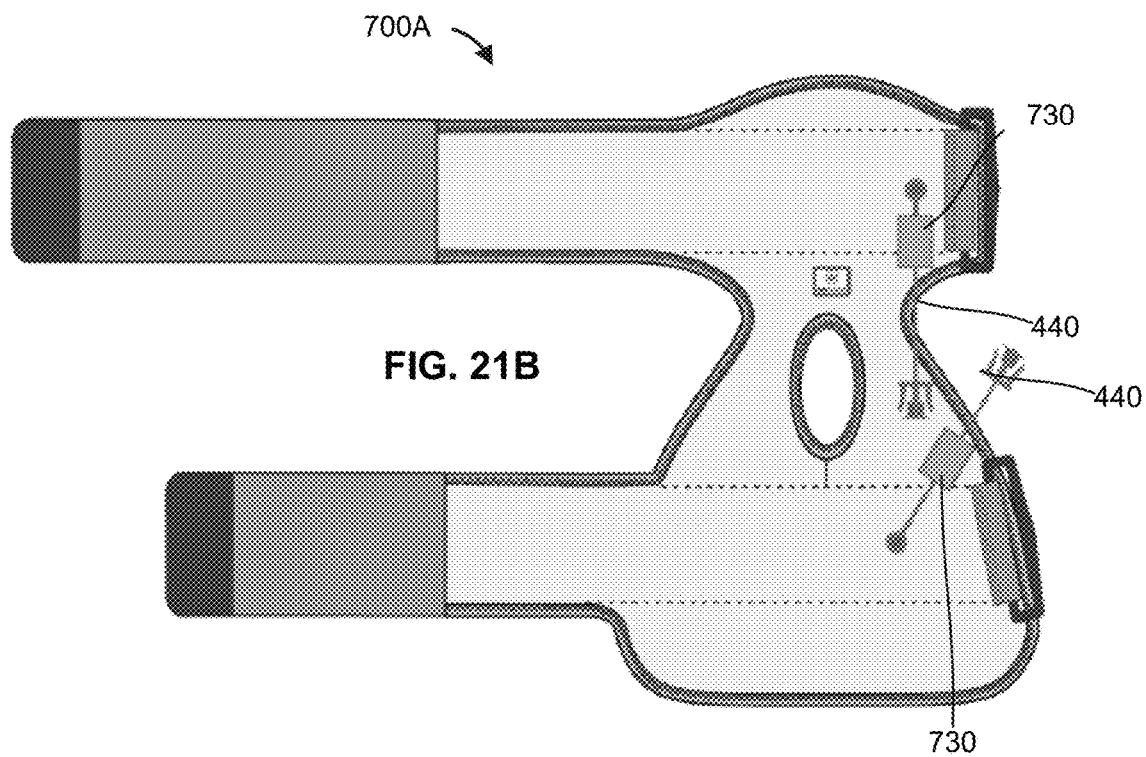
FIG. 21B is an outside view of the ankle/foot wearable system in accordance with some embodiments of the present disclosure.

FIGS. 21A and 21B include another exemplary embodiment of an ankle/foot wearable system 700A, including another design with similar features. For example, the ankle/foot wearable system 700A may further include channels 730. The channels 730 may be wire management features configured to receive and route a wire connector between the electrode connectors 728 and an electrotherapeutic device. For example, each channel 730 may be positioned adjacent to a respective electrode connector 728 and configured to route intermediate wire 440 from the electrode connector 728 to another position (e.g., beneath or above the garment 710).

FIGS. 22 and 23 further illustrate the ankle/foot wearable system 700 being worn by a user. The garment 710 is held in place by the elastic straps 716 such that the electrodes 724, 725 are positioned at a target area—the area at or above the ankle and a portion of the foot, respectively. The elastic straps 716 also provide compression directly over the electrodes 724 and 725 to provide better electrical conduction through the skin. The user's heel is positioned in the heel hole 726. Intermediate wires 440 are connected to the electrode connectors 728 and are held down by the elastic straps 716. The second wire connectors 444 are easily accessible for functional connection to an electrotherapeutic device according to disclosed embodiments. FIG. 22 is an illustration of a right leg and foot of a user and FIG. 23 is an illustration of a left leg and foot of a user. As described, the application area 712 may be generally symmetrical across a vertical center line through the heel hole 726 such that the ankle/foot wearable system 700 is configured to be worn on either the right or left leg and foot as shown.

Figure 24:
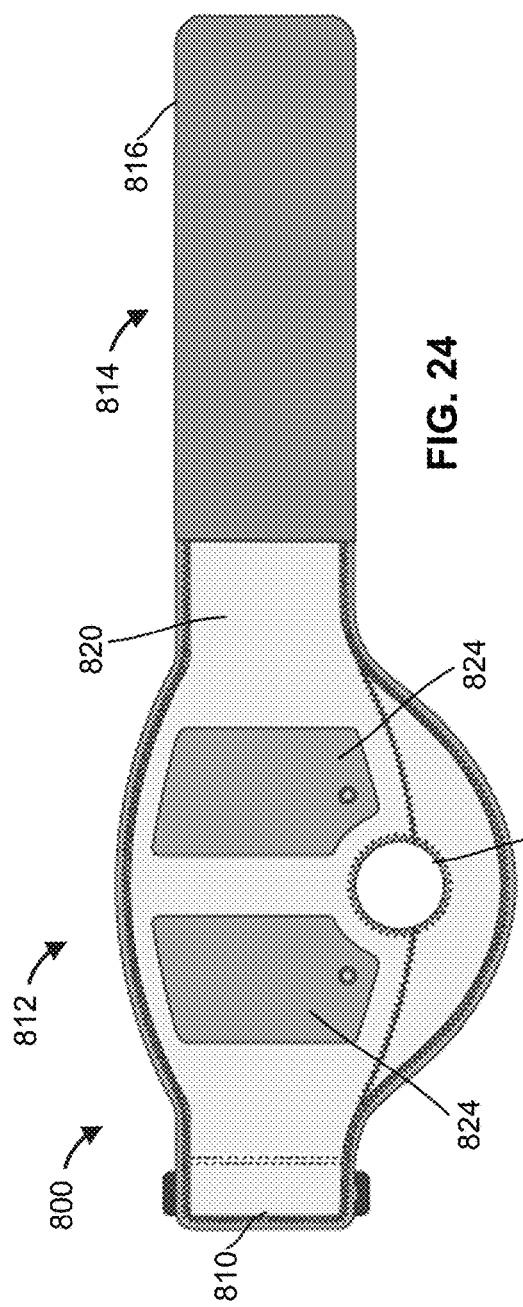
FIG. 24 is an inside view of an elbow wearable system in accordance with some embodiments of the present disclosure.
Figure 25:
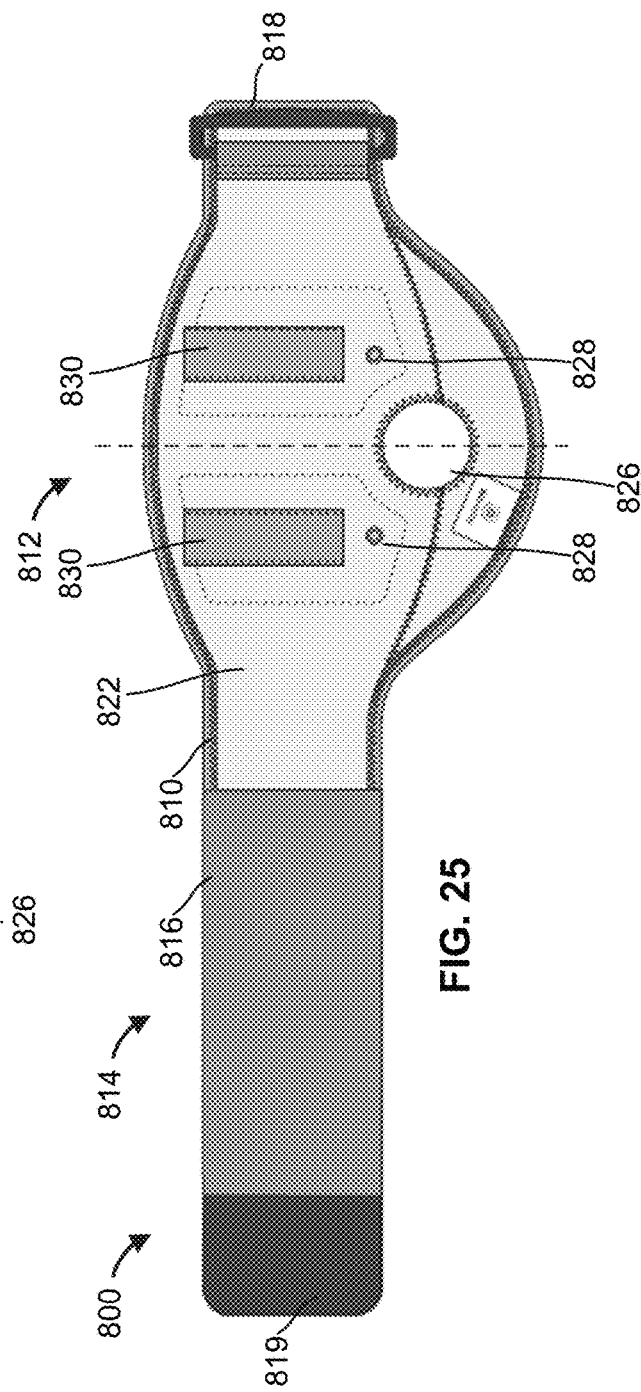
FIG. 25 is an outside view of the elbow wearable system in accordance with some embodiments of the present disclosure.

FIGS. 24 and 25 are front and back views of an exemplary embodiment of the elbow wearable system 800. The elbow wearable system 800 may include a garment 810. The garment 810 may be constructed as a flexible wrap configured to be worn around an elbow area of a user. The garment 810 may include a fabric material and include an application area 812 configured to be positioned adjacent to an elbow area of a user. The garment 810 may further include attachment mechanism 814 in the form of an elastic strap 816 attached to the application area 812 for securing the garment 810 in place. The garment 810 may also include one or more loops or rings 818 for routing the elastic strap 816 and a fastener 819 (e.g., hook and loop fastener) for securing the elastic strap 816 to the application area 812. It is also contemplated that garment 810 may be constructed as a sleeve, and made of stretch material, such that garment 810 can be pulled onto the elbow of a user, without the need to wrap garment 810, where the stretch material secures garment 810 into place. For example, in some embodiments, the attachment mechanism 814 may be a built-in elastic property, such as may be present in a sleeve embodiments, and not necessarily an additional feature such as strap 816, loops 818, and/or fastener 819.

The garment 810 may include an interior surface 820 configured to contact the user and an opposite exterior surface 822. The elbow wearable system 800 may further comprise one or more electrodes 824 on the interior surface 820 and configured to contact the user. The electrodes 824 may be built-in conductive fabric electrodes, for example. The one or more electrodes 824 may include two electrode pads positioned in the application area 812 and configured to contact an elbow area of a user. In an exemplary embodiment, the one or more electrodes 824 are positioned on opposing sides of an elbow hole 826 built-in to the garment 810 to provide two spaced-apart electrotherapeutic locations for the elbow wearable system 800. The electrodes 824 may be rectangular-shaped with cutout-portions 827 configured to follow an outline of the elbow hole 826. In this way, the electrodes 824 may be positioned such that treatment is not applied directly to the elbow joint (e.g., the bony portion at the corner of the elbow). While two electrodes 824 are shown, it should be understood that disclosed embodiments are not limited to any particular number of electrodes.

The garment 810 may further include at least one electrode connector 828. The garment 810 may include an electrode connector 828 for each electrode 824. The electrode connector 828 may include a mechanical and electrical connection point for the respective electrode 824. In an exemplary embodiment, the electrode connector 828 is a snap connector, such as a male snap element configured to mate with a female snap element. The electrode connector 828 may include a conductive material (e.g., metal) such that a functional electrical connection may be established with the electrode 824 via the electrode connector 828. In an exemplary embodiment, the electrode connector 828 may have a non-conductive coating on the bottom side of the snap connector (e.g., rivet) that is exposed on the face of the electrode 824. This non-conductive coating helps to prevent the patient from feeling a hot spot or stinging sensation at the location of the snap connector. In an exemplary embodiment, the electrode connectors 828 are positioned on the exterior surface 822.

In an exemplary embodiment, the electrode connectors 828 are positioned on the exterior surface 822 above or below the location of the compression material (e.g., memory foam) which sits beneath and raises the electrode surface above the interior surface 820. The conductive surface of each electrode 824 may continue above or below the memory foam directly onto the interior surface 820. The electrode connector 828 may be placed at this location through the electrode surface, spaced from the compression material. A nonconductive material may be applied to cover up the portion of the conductive fabric and the electrode connector 828 that sits recessed below the compression material. This type of construction eliminates stinging and leaves a smooth raised surface for the conductive electrode 824.

The garment 810 may further include channels 830. The channels 830 may be wire management features configured to receive and route a wire connector between the electrode connectors 828 and an electrotherapeutic device. For example, each channel 830 may be positioned adjacent to a respective electrode connector 828 and configured to route intermediate wire 440 from the electrode connector 828 to another position (e.g., beneath or above the garment 810). The first wire connector 442 of each intermediate wire 440 may be configured to attach to a respective electrode connector 828.

Figure 26:
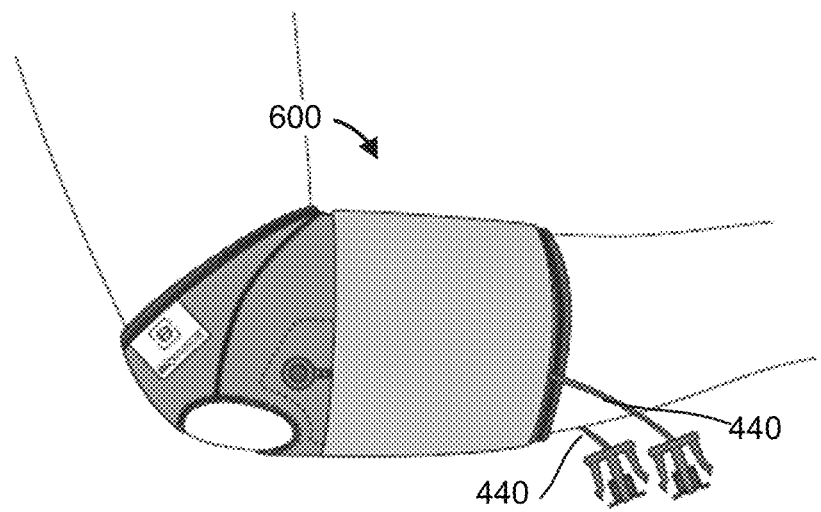
FIG. 26 is a depiction of the elbow wearable system on a right arm of a user in accordance with some embodiments of the present disclosure.
Figure 27:
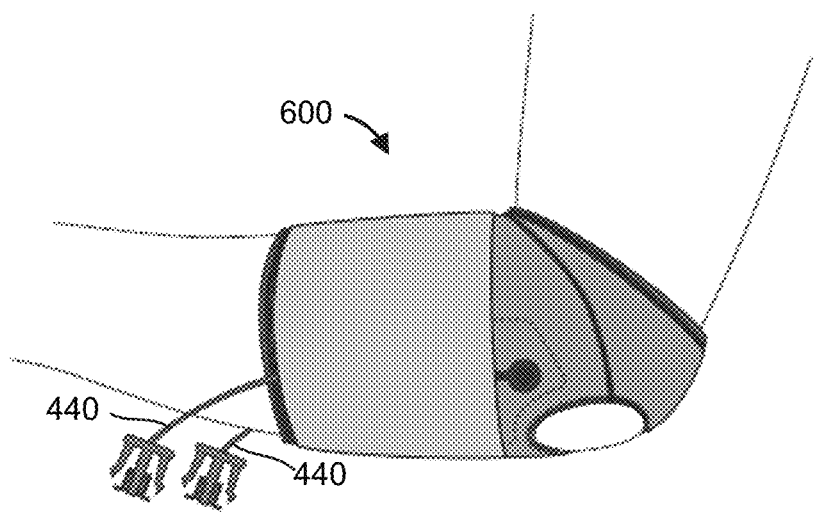
FIG. 27 is a depiction of the elbow wearable system on a left arm of a user in accordance with some embodiments of the present disclosure.

FIGS. 26 and 27 further illustrate the elbow wearable system 800 being worn by a user. The garment 810 is held in place by the elastic strap 816 such that the electrodes 824 are positioned at a target area—a forearm area adjacent to the user's elbow, for example. The elastic strap 816 serves the dual of purpose of securing the garment 810 in the proper position around the elbow and in addition provides compression directly over the electrodes 824 and as a result it provides better electrical conduction through the skin. The user's elbow joint is positioned in the elbow hole 826. Intermediate wires 440 are connected to the electrode connectors 828 and routed through the channels 830. The second wire connectors 444 are easily accessible for functional connection to an electrotherapeutic device according to disclosed embodiments. FIG. 26 is an illustration of a right arm of a user and FIG. 27 is an illustration of a left arm of a user. The application area 812 may be generally symmetrical across a vertical center line through the elbow hole 826 such that the elbow wearable system 800 is configured to be worn on either the right or left arm as shown.

Figure 28:
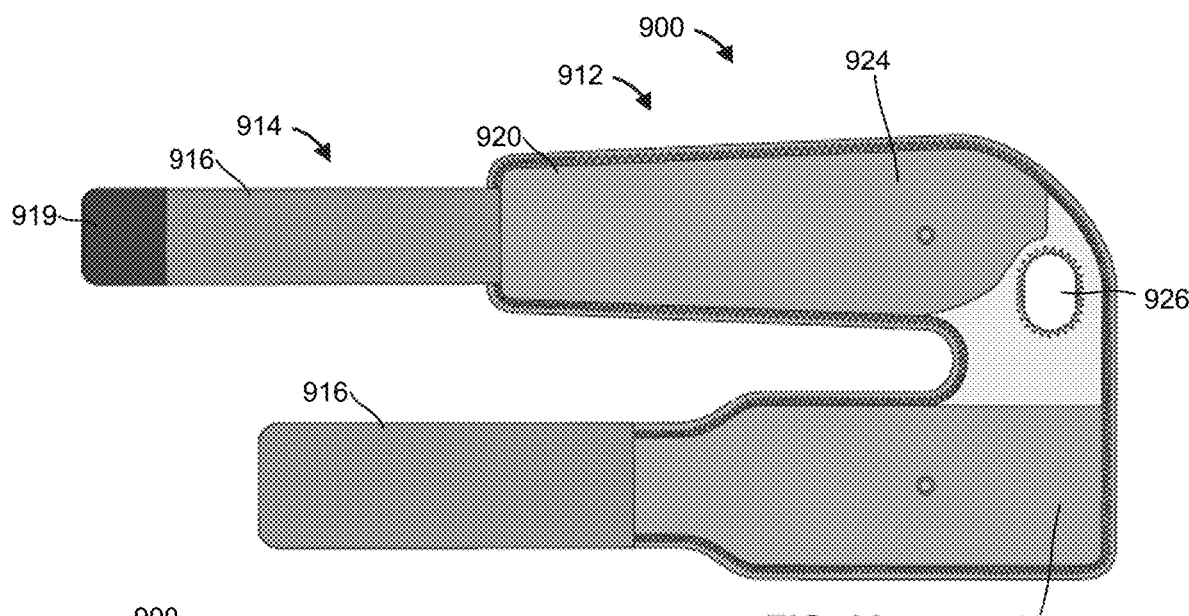
FIG. 28 is an inside view of a wrist/hand wearable system in accordance with some embodiments of the present disclosure.
Figure 29:
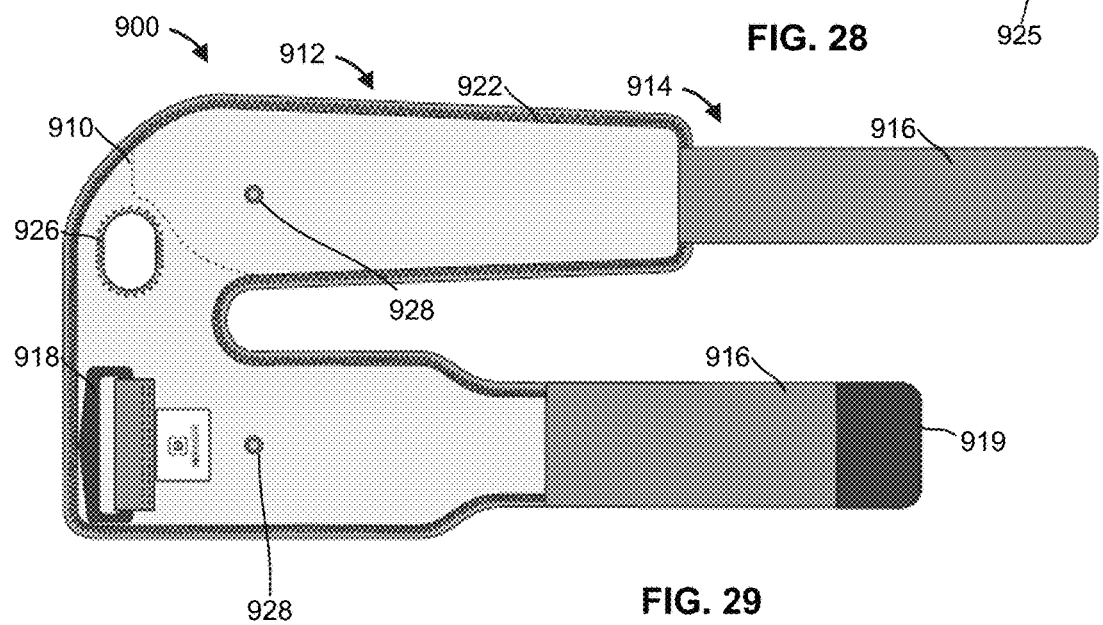
FIG. 29 is an outside view of the wrist/hand wearable system in accordance with some embodiments of the present disclosure.

FIGS. 28 and 29 are front and back views of an exemplary embodiment of the wrist/hand wearable system 900. The wrist/hand wearable system 900 may include a garment 910. The garment 910 may be constructed as a flexible wrap configured to be worn around at least a portion of the wrist and/or hand of a user. The garment 910 may include a fabric material and include an application area 912 configured to be positioned adjacent to a wrist and hand area of a user. The garment 910 may further include attachment mechanism 914 in the form of one or more elastic straps 916 attached to the application area 912 for securing the garment 910 in place. Both elastic straps 916 also provide compression directly over the electrodes 924 and 925 and as a result it provides better electrical conduction through the skin. The garment 910 may also include one or more loops or rings 918 for routing a respective elastic strap 916 and a fastener 919 (e.g., hook and loop fastener) for securing each elastic strap 916 to the application area 912. It is also contemplated that garment 910 may be constructed as a sleeve, and made of stretch material, such that garment 910 can be pulled onto the hand/wrist of a user, without the need to wrap garment 910, where the stretch material secures garment 910 into place. For example, in some embodiments, the attachment mechanism 914 may be a built-in elastic property, such as may be present in a sleeve embodiment, and not necessarily an additional feature such as strap 916, loops 918, and/or fastener 919.

The garment 910 may include an interior surface 920 configured to contact the user and an opposite exterior surface 922. The wrist/hand wearable system 900 may further comprise one or more electrodes 924, 925 on the interior surface 920 and configured to contact the user. The electrodes 924, 925 may be built-in conductive fabric electrodes, for example. The one or more electrodes 924, 925 may include two electrode pads positioned in the application area 912 and configured to contact a wrist and/or hand area of user. While two electrodes 924, 925 are shown, it should be understood that disclosed embodiments are not limited to any particular number of electrodes.

In an exemplary embodiment, each electrode 924, 925 is configured as a rectangular strip configured to wrap around a portion of the user to provide a wide contact area. For example, the electrode 924 may be configured to wrap just at or above a wrist of a user and the electrode 925 may be configured to wrap around a portion of the hand of the user.

The garment 910 may further include a thumb hole 926 to receive and accommodating a thumb of the user. The thumb hole 926 may be positioned between and to one end of the electrodes 924, 925. The garment 910 may include a C-shape with a lower portion for wrapping around the hand of a user and a top portion for wrapping around the wrist of the user.

The garment 910 may further include at least one electrode connector 928. The garment 910 may include an electrode connector 928 for each electrode 924. The electrode connector 928 may include a mechanical and electrical connection point for the respective electrode 924. In an exemplary embodiment, the electrode connector 928 is a snap connector, such as a male snap element configured to mate with a female snap element. The electrode connector 928 may include a conductive material (e.g., metal) such that a functional electrical connection may be established with the electrode 924 via the electrode connector 928. In an exemplary embodiment, the electrode connector 928 may have a non-conductive coating on the bottom side of the snap connector (e.g., rivet) that is exposed on the face of the electrode 924. This non-conductive coating helps to prevent the patient from feeling a hot spot or stinging sensation at the location of the snap connector. In an exemplary embodiment, the electrode connectors 928 are positioned on the exterior surface 922.

In an exemplary embodiment, the electrode connectors 928 are positioned on the exterior surface 922 above or below the location of the compression material (e.g., memory foam) which sits beneath and raises the electrode surface above the interior surface 920. The conductive surface of each electrode 924 may continue above or below the memory foam directly onto the interior surface 920. The electrode connector 928 may be placed at this location through the electrode surface, spaced from the compression material. A nonconductive material may be applied to cover up the portion of the conductive fabric and the electrode connector 928 that sits recessed below the compression material. This type of construction eliminates stinging and leaves a smooth raised surface for the conductive electrode 924.

The garment 910 may be configured to operate in conjunction with one or more of the intermediate wires 440. The intermediate wires 440 may be positioned to extend from each electrode connector 928 to another position (e.g., beneath or above the garment 910). The first wire connector 442 of each intermediate wire 440 may be configured to attach to a respective electrode connector 928. The electrode connectors 928 may be positioned to be covered by the elastic straps 916 such the elastic straps may act as a hold-down for at least a portion of the intermediate wires 440.

Figure 30:
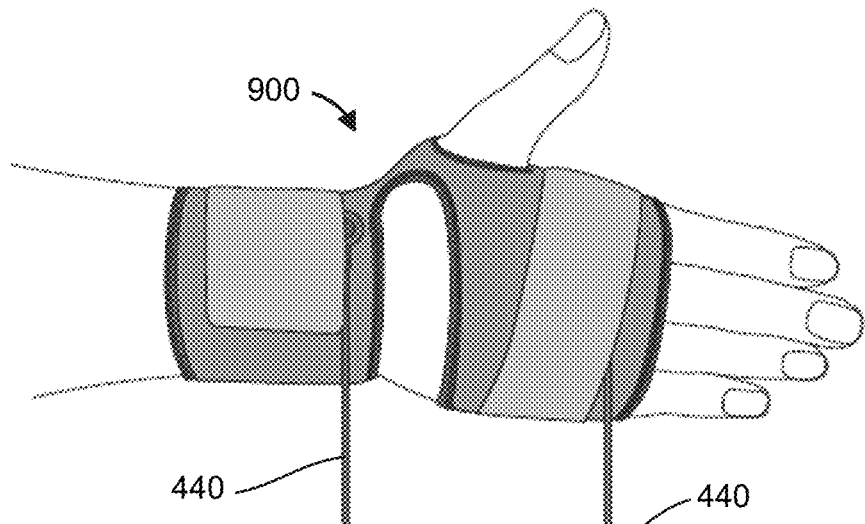
FIG. 30 is a depiction of the wrist/hand wearable system on a right hand of a user in accordance with some embodiments of the present disclosure.
Figure 31:
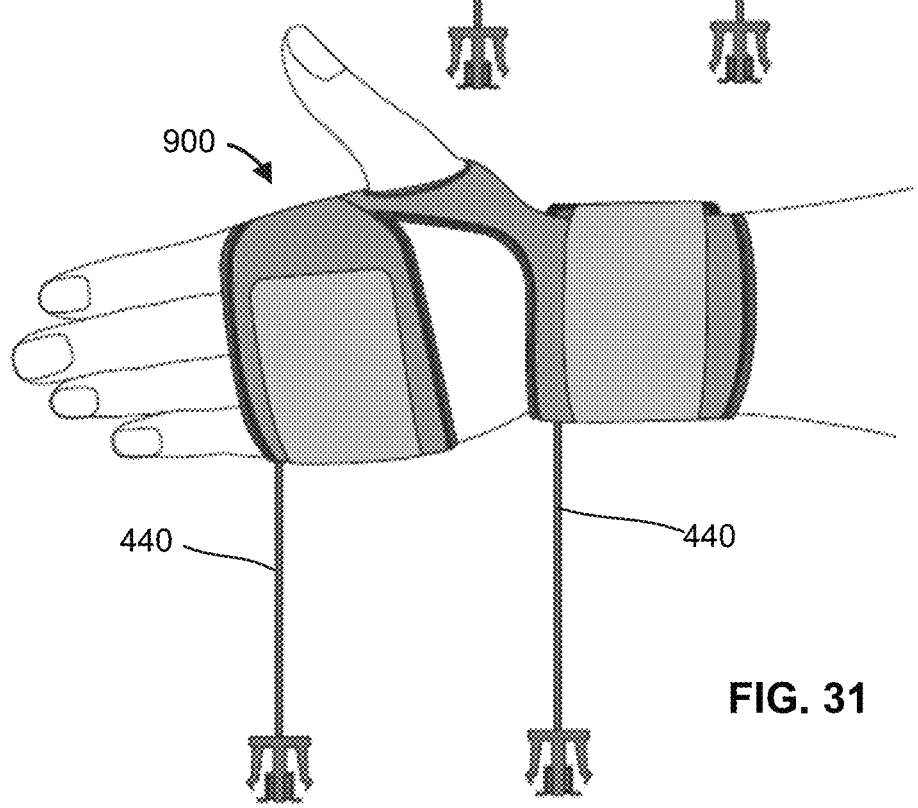
FIG. 31 is a depiction of the wrist/hand wearable system on a left hand of a user in accordance with some embodiments of the present disclosure.

FIGS. 30 and 31 further illustrate the wrist/hand wearable system 900 being worn by a user. The garment 910 is held in place by the elastic straps 916 such that the electrodes 924, 925 are positioned at a target area—the area at or above the wrist and a portion of the hand, respectively. The user's thumb is positioned in the thumb hole 926. Intermediate wires 440 are connected to the electrode connectors 928 and are held down by the elastic straps 916. The second wire connectors 444 are easily accessible for functional connection to an electrotherapeutic device according to disclosed embodiments. FIG. 30 is an illustration of a right wrist and hand of a user, and FIG. 31 is an illustration of a left wrist and hand of a user. The wrist/hand wearable system 900 is configured to be worn on either the right or left hand and wrist as shown.

FIGS. 32A and 32B are front and back views of an exemplary embodiment of the shoulder wearable system 1000. The shoulder wearable system 1000 may include a garment 1010. The garment 1010 may be constructed as a flexible wrap configured to be worn around at least a portion of the shoulder and/or upper arm of a user. The garment 1010 may include a fabric material and include an application area 1012 configured to be positioned adjacent to a shoulder area of a user. The garment 1010 may further include attachment mechanism 1014 in the form of one or more elastic straps 1016, 1036 attached to the application area 1012 for securing the garment 1010 in place. The secondary elastic strap 1026 provides compression directly over the electrodes 1024 and as a result it provides better electrical conduction through the skin. The garment 1010 may also include one or more loops or rings 1018, 1038 for routing a respective elastic strap 1016, 1036 and a fastener 1019, 1039 (e.g., hook and loop fastener) for securing each elastic strap 1016, 1036 to the application area 1012. In an exemplary embodiment, the strap 1016 wraps around a neck/opposite shoulder of the wearer and the strap 1036 wraps around an upper arm of the applied shoulder. It is also contemplated that garment 1010 may be constructed as a sleeve, and made of stretch material, such that garment 1010 can be pulled onto the arm/shoulder of a user, without the need to wrap garment 1010, where the stretch material secures garment 1010 into place. For example, in some embodiments, the attachment mechanism 1014 may be a built-in elastic property, such as may be present in a sleeve embodiments, and not necessarily an additional feature such as straps 1016, 1036, loops 1018, 1038, and/or fastener 1019, 1039.

The garment 1010 may include an interior surface 1020 configured to contact the user and an opposite exterior surface 1022. The shoulder wearable system 1000 may further comprise one or more electrodes 1024 on the interior surface 1020 and configured to contact the user. The electrodes 1024 may be built-in conductive fabric electrodes, for example. The one or more electrodes 1024 may include two electrode pads positioned in the application area 1012 and configured to contact a targeted portion of a shoulder of user. While two electrodes 1024 are shown, it should be understood that disclosed embodiments are not limited to any particular number of electrodes. The electrodes 1024 may include any shape to target application to a shoulder, such as having at least one curved edge in a semi-circle shape.

The garment 1010 may further include a protective portion 1026 on the exterior surface 1026. The protective portions 1026 may be attached to portions of the attachment mechanism 1014 and be centered opposite the electrodes 1024.

The garment 1010 may further include at least one electrode connector 1028. The garment 1010 may include an electrode connector 1028 for each electrode 1024. The electrode connector 1028 may include a mechanical and electrical connection point for the respective electrode 1024. In an exemplary embodiment, the electrode connector 1028 is a snap connector, such as a male snap element configured to mate with a female snap element. The electrode connector 1028 may include a conductive material (e.g., metal) such that a functional electrical connection may be established with the electrode 1024 via the electrode connector 1028. In an exemplary embodiment, the electrode connector 1028 may have a non-conductive coating on the bottom side of the snap connector (e.g., rivet) that is exposed on the face of the electrode 1024. This non-conductive coating helps to prevent the patient from feeling a hot spot or stinging sensation at the location of the snap connector. In an exemplary embodiment, the electrode connectors 1028 are positioned on the exterior surface 1022.

In an exemplary embodiment, the electrode connectors 1028 are positioned on the exterior surface 1022 above or below the location of the compression material (e.g., memory foam) which sits beneath and raises the electrode surface above the interior surface 1020. The conductive surface of each electrode 1024 may continue above or below the memory foam directly onto the interior surface 1020. The electrode connector 1028 may be placed at this location through the electrode surface, spaced from the compression material. A nonconductive material may be applied to cover up the portion of the conductive fabric and the electrode connector 1028 that sits recessed below the compression material. This type of construction eliminates stinging and leaves a smooth raised surface for the conductive electrode 1024.

The garment 1010 may be configured to operate in conjunction with one or more of the intermediate wires 440. The intermediate wires 440 may be positioned to extend from each electrode connector 1028 to another position (e.g., beneath or above the garment 1010). The first wire connector 442 of each intermediate wire 440 may be configured to attach to a respective electrode connector 1028. The electrode connectors 1028 may be positioned to be covered by the elastic straps 1016 such the elastic straps may act as a hold-down for at least a portion of the intermediate wires 440.

FIGS. 33A and 33B include another exemplary embodiment of a shoulder wearable system 1000A, including another design with similar features. For example, the shoulder wearable system 1000A may include rectangular electrodes 1024A and an alternative protective portion 1026A.

FIGS. 34 and 35 are front and back views of an embodiment of the head/neck wearable system 1100. The knee wearable system 1100 may include a garment 1110. The garment 1110 may be constructed as a flexible wrap configured to be worn around a head/neck area of a user. The garment 1110 may include a fabric material and include an application area 1112 configured to be positioned adjacent to a head and/or neck area of a user. The garment 1110 may further include attachment mechanism 1114 in the form of an elastic strap 1116 attached to the application area 1112 for securing the garment 1110 in place. The garment 1110 may also include a first fastener 1118 and a second fastener 1119 (e.g., hook and loop fastener) for securing the elastic strap 1116 to the application area 1112. The elastic strap 1116 also provides compression directly over the electrodes 1124 and as a result it provides better electrical conduction through the skin. It is also contemplated that garment 1110 may be constructed as a sleeve, and made of stretch material, such that garment 1110 can be pulled onto the head/neck area of a user, without the need to wrap garment 1110, where the stretch material secures garment 1110 into place. For example, in some embodiments, the attachment mechanism 1114 may be a built-in elastic property, such as may be present in a sleeve embodiment, and not necessarily an additional feature such as strap 1116 and/or fasteners 1118, 1119.

The garment 1110 may include an interior surface 1120 configured to contact the user and an opposite exterior surface 1122. The neck wearable system 1100 may further comprise one or more electrodes 1124 on the interior surface 1120 and be configured to contact the user. The electrodes 1124 may be built-in conductive fabric electrodes, for example. The one or more electrodes 1124 may include two electrode pads positioned in the application area 1112 and configured to contact a head and/or neck area of a user. In an exemplary embodiment, the one or more electrodes 1124 may be configured to contact the back of a user's neck, just above the collar. In another example, the electrodes 1124 may be configured to contact the back, top or forehead of the user. The electrodes 1124 may be circular shaped. While two electrodes 1124 are shown, it should be understood that disclosed embodiments are not limited to any particular number, shape or size of electrodes.

Figure 36:
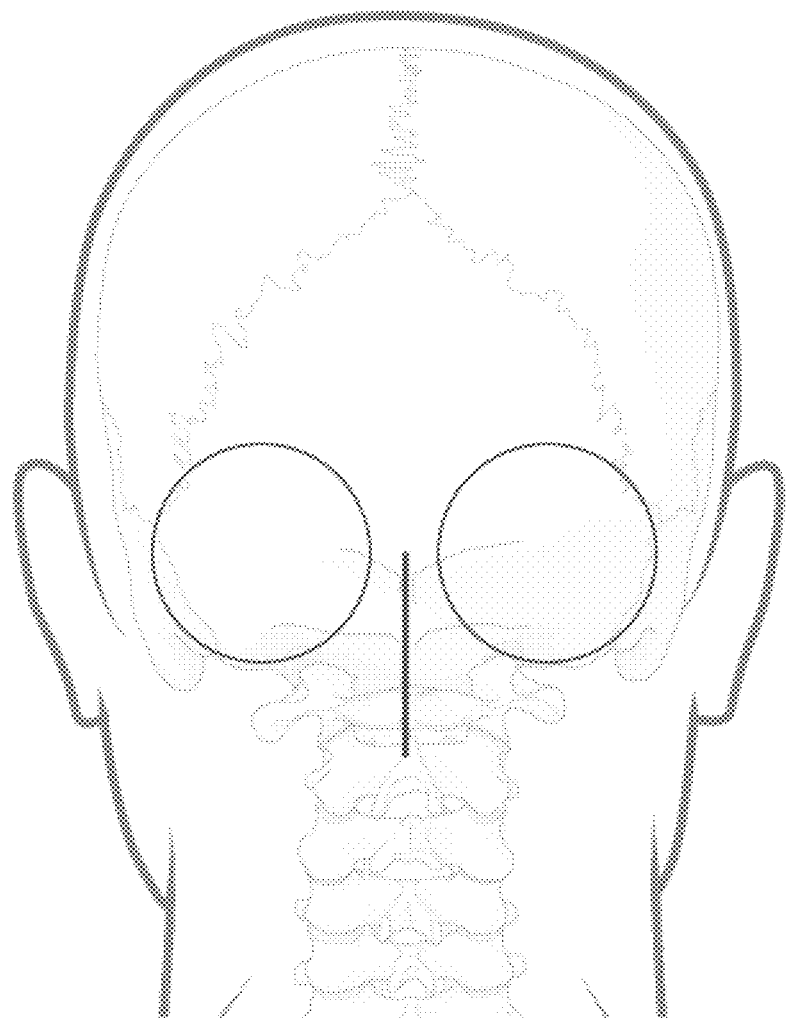
FIG. 36 is a diagram showing an example placement of electrodes using the head/neck wearable system.

In some embodiments, the head/neck wearable system 1100 may be used to reduce pain that results from headaches including cervicogenic headaches which appear to transform into migraines; chronic cervicalgia, occipital neuralgia and pain which originates in the posterior of the neck and travels up into the head. In an exemplary embodiment, the electrodes 1124 are placed bilaterally at the occiput on either side of the cervical spine on the posterior of the skull (as shown in the illustration of FIG. 36). The inside edges of the electrodes 1124 may be about 0.5" apart from each other, which may be a minimum distance between the electrodes 1124. Edges of the electrodes 1124 do not touch. In some examples, users need to shave the hair line at the base of the skull so electrodes can be placed on clean intact skin. Patients can rest their head on a pillow with their neck bent slightly forward. Generally having the tissue be a little taut in the region treated allows for deeper penetration of the active electrical field. In one example, each treatment is 30 minutes in duration. Initially, 3 treatments are performed with 30 minutes to 2 hours in between each treatment.

The garment 1110 may further include at least one electrode connector 1128. The garment 1110 may include an electrode connector 1128 for each electrode 1124. The electrode connector 1128 may include a mechanical and electrical connection point for the respective electrode 1124. In an exemplary embodiment, the electrode connector 1128 is a snap connector, such as a male snap element configured to mate with a female snap element. The electrode connector 1128 may include a conductive material (e.g., metal) such that a functional electrical connection may be established with the electrode 1124 via the electrode connector 1128. In an exemplary embodiment, the electrode connector 1128 may have a non-conductive coating on the bottom side of the snap connector (e.g., rivet) that is exposed on the face of the electrode 1124. This non-conductive coating helps to prevent the patient from feeling a hot spot or stinging sensation at the location of the snap connector. In an exemplary embodiment, the electrode connectors 1128 are positioned on the exterior surface 1122.

In an exemplary embodiment, the electrode connectors 1128 are positioned on the exterior surface 1122 above or below the location of the compression material (e.g., memory foam) which sits beneath and raises the electrode surface above the interior surface 1120. The conductive surface of each electrode 1124 may continue above or below the memory foam directly onto the interior surface 1120. The electrode connector 1128 may be placed at this location through the electrode surface, spaced from the compression material. A nonconductive material may be applied to cover up the portion of the conductive fabric and the electrode connector 1128 that sits recessed below the compression material. This type of construction eliminates stinging and leaves a smooth raised surface for the conductive electrode 1124.

The garment 1110 may be configured to operate in conjunction with one or more of the intermediate wires 440. The intermediate wires 440 may be positioned to extend from each electrode connector 1128 to another position (e.g., beneath or above the garment 1110). The first wire connector 442 of each intermediate wire 440 may be configured to attach to a respective electrode connector 1128. The electrode connectors 1128 may be positioned to be covered by the elastic straps 1116 such the elastic straps may act as a hold-down for at least a portion of the intermediate wires 440.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

While various embodiments have been described, it is to be understood that the embodiments described are illustrative only and that the scope of the subject matter is to be accorded a full range of equivalents, many variations and modifications naturally occurring to those of skill in the art from a perusal hereof

What is claimed is:

1. A wearable garment, comprising:
   a flexible material configured to wrap around a portion of a user's body, the flexible material comprising:
      an interior surface configured to contact the user's body, and
      an opposite exterior surface;
   a tightening strap configured to hold the flexible material in place on the user's body;
   a first electrode positioned at the interior surface and configured to contact a targeted part of the user's body with a conductive fabric;
   a second electrode positioned at the interior surface and configured to contact the targeted part of the user's body with the conductive fabric;
   a first electrode connector positioned at the exterior surface and operably connected to the first electrode; and
   a second electrode connector positioned at the exterior surface and operably connected to the second electrode,
   wherein the first and second electrodes are configured to deliver a therapeutic signal from an electrotherapeutic device via the first and second electrode connectors, wherein the first electrode connector and the second electrode connector each comprise a stud on the exterior surface and a rivet on the interior surface, and wherein the rivet includes a coating of non-conductive material.

2. The wearable garment of claim 1, wherein the first electrode and the second electrode include a smooth raised portion to contact the user's body and a lower portion that does not contact the user's body.

3. The wearable garment of claim 2, wherein the first electrode connector and the second electrode connector are coupled to the fabric of the respective first electrode and second electrode at the lower portion.

4. The wearable garment of claim 3, wherein the fabric of the first electrode and the second electrode is positioned over a compression material, wherein the compression material includes a thickness that forms the raised portion of the first electrode and the second electrode.

5. The wearable garment of claim 1, wherein the conductive fabric of the first electrode and the second electrode is flexible to wrap around the targeted part of the user's body.

6. The wearable garment of claim 1, wherein the flexible material comprises an application area and an attachment mechanism for securing the application area to the user's body.

7. The wearable garment of claim 6, wherein the flexible material is configured to be separately worn on both right and left limbs.

8. The wearable garment of claim 6, wherein the attachment mechanism is an elastic strap, and wherein the elastic strap provides compression directly over the application area to maintain electrical contact with the targeted part of the user's body.

9. The wearable garment of claim 6, wherein the flexible material is configured as a sleeve and wherein the attachment mechanism is an elastic property of the flexible material.

10. The wearable garment of claim 1, further comprising a wire management feature configured to route a wire connected to the first or second electrode connector.

11. The wearable garment of claim 10, wherein the wire management feature comprises a channel configured to receive a portion of a wire.

12. The wearable garment of claim 1, wherein the flexible material is shaped and configured as a belt to wrap around a user's waist.

13. The wearable garment of claim 1, wherein the flexible material is shaped and configured to wrap around a user's knee or elbow and further comprising a hole for locating the proper positioning of the wearable garment.

14. The wearable garment of claim 13, wherein the targeted parts of the user's body include an ankle and foot or a wrist and hand.

15. A wearable system, comprising:
a garment, comprising:
a flexible material configured to wrap around a portion of a user's body, the flexible material comprising:
an interior surface configured to contact the user's body, and
an opposite exterior surface;
a tightening strap configured to hold the flexible material in place on the user's body;
a first electrode positioned at the interior surface and configured to contact a targeted part of the user's body with a conductive fabric;
a second electrode positioned at the interior surface and configured to contact the targeted part of the user's body with the conductive fabric;
a first electrode connector positioned at the exterior surface and operably connected to the first electrode; and
a second electrode connector positioned at the exterior surface and operably connected to the second electrode;
wherein the first electrode connector and the second electrode connector each comprise a stud on the exterior surface and a rivet on the interior surface, and wherein the rivet includes a coating of non-conductive material;
an electrotherapeutic device configured to deliver a therapeutic signal to the first and second electrodes via the first and second electrode connectors.

16. The wearable system of claim 15, wherein the first electrode and the second electrode include a smooth raised portion to contact the user's body and a lower portion that does not contact the user's body.

17. The wearable system of claim 16, wherein the first electrode connector and the second electrode connector are coupled to the fabric of the respective first electrode and the second electrode at the lower portion.

18. The wearable system of claim 17, wherein the fabric of the first electrode and the second electrode is positioned over a compression material, wherein the compression material includes a thickness that forms the raised portion of the first electrode and the second electrode.

19. The wearable system of claim 15, wherein the tightening strap is an elastic strap, and wherein the elastic strap provides compression directly over the first and second electrodes to maintain electrical contact with the targeted part of the user's body.

20. The wearable system of claim 19, wherein the garment further comprises a wire management feature configured to route the intermediate wire between the electrotherapeutic device and the first electrode connector.

21. A method for providing therapeutic electric current to a treatment site of a patient comprising the steps of:
providing a flexible garment comprising a first electrode and a second electrode each having a conductive fabric;
providing an electrotherapeutic device operably connected to the first electrode and the second electrode with a respective first electrode connector and a second electrode connector, wherein the first electrode connector and the second electrode connector each comprise a stud on the exterior surface and a rivet on the interior surface, and wherein the rivet includes a coating of non-conductive material;
positioning the flexible garment with respect to a user's body such that the first electrode and the second electrode are each in contact with a targeted part of the user's body;
forming a therapeutic signal configured to reduce pain at a treatment site by simultaneously sending a first signal from the first electrode to the second electrode and sending a second signal from the second electrode to the first electrode, and then simultaneously sending the first signal from the second electrode back to the first electrode and the second signal from the first electrode back to the second electrode.

22. The method of claim 21, wherein positioning the flexible garment with respect to the user's body comprises pulling a sleeve over a part of the body and sliding the sleeve to a desired position.

* * * * *